US012807569B2

(12) United States Patent
Nichols

(10) Patent No.: US 12,807,569 B2
(45) Date of Patent: Nov. 24, 2026

(54) COMPOUNDS AND METHODS FOR TREATING 5-HT2 RESPONSIVE CONDITIONS

(71) Applicant: Board of Supervisors of Louisiana State University and Agricultural and Mechanical College, Baton Rouge, LA (US)

(72) Inventor: Charles Nichols, New Orleans, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 369 days.

(21) Appl. No.: 18/291,874

(22) PCT Filed: Jul. 26, 2022

(86) PCT No.: PCT/US2022/704139
§ 371 (c)(1),
(2) Date: Jan. 24, 2024

(87) PCT Pub. No.: WO2023/010000
PCT Pub. Date: Feb. 2, 2023

(65) Prior Publication Data

US 2024/0327347 A1 Oct. 3, 2024

Related U.S. Application Data

(60) Provisional application No. 63/225,755, filed on Jul. 26, 2021.

(51) Int. Cl.

| | |
|---|---|
| ***C07D 209/16*** | (2006.01) |
| ***A61K 31/137*** | (2006.01) |
| ***A61K 31/4045*** | (2006.01) |
| ***A61P 29/00*** | (2006.01) |
| ***C07C 217/60*** | (2006.01) |

(52) U.S. Cl.
CPC .......... *C07D 209/16* (2013.01); *A61K 31/137* (2013.01); *A61K 31/4045* (2013.01); *A61P 29/00* (2018.01); *C07C 217/60* (2013.01)

(58) Field of Classification Search
CPC ..... C07D 209/16; A61P 29/00; A61K 31/137; A61K 31/4045; C07C 217/60
See application file for complete search history.

(56) References Cited

U.S. PATENT DOCUMENTS

2021/0137908 A1 5/2021 Kristensen et al.

FOREIGN PATENT DOCUMENTS

| | | | |
|---|---|---|---|
| CA | 3136153 | | 10/2020 |
| WO | WO1993000333 | A1 | 1/1993 |
| WO | WO2018060732 | † | 4/2018 |
| WO | WO2018064465 | † | 4/2018 |
| WO | WO2020210623 | A1 | 10/2020 |
| WO | WO2020210823 | A1 | 10/2020 |

OTHER PUBLICATIONS

Ruggli et al., 28 Helvetica Chimica Acta 674-90 (1945) (Year: 1945).*

Database Registry [Online], Chemical Abstract Service, Columbus, Ohio, US; Oct. 15, 2006 (Oct. 15, 2006), XP093276017, Database accession No. 910382-80-8.

Database STN [Online], Chemical Abstract Service, Columbus, Ohio, US; Oct. 15, 2006 (Oct. 15, 2006), XP093276018, Database accession No. 910398-56-0.

Ruggle, P. et. et. Über m-Phenylen-β,β-di-äthylbromid; ein Beitrag zur Desaminierung aliphatischer Diamine. (56. Mitteilung über Stickstoff-Heterocyclen) (on m-phenylene-β,β-diethyl bromide; a contribution to the deamination of aliphatic diamines. (56th report on nitrogen heterocycles). Helvetica Chimica Acta, A61P29/00, vol. 28, No. 1, Jan. 1, 1945 (Jan. 1, 1945), pp. 674-690, XP093276011, Hoboken, USA.

Bear, M. F. et al. Neuroscience: Exploring the Brain. 4th edition, Jones and Bartlett Learning (2016).

Berge, S. M. et al. Pharmaceutical Salts. J. Pharmaceutical Sciences, 66:1-19 (1977).

Diagnostic and Statistical Manual of Mental Disorders (DSM-V), American Psychiatric Association, 5th Edition, 992 pages (2013).

Diagnostic and Statistical Manual of Mental Disorders (OSM-IV), American Psychiatric Press, 4th Edition, 915 pages (1994).

Hayes, Sh. Book Review: Remington: The Science and Practice of Pharmacy, vol. I and vol. II, 22nd edition, Philadelphia, 2012, review publixhed in J. Med. Lib. Assoc., 102(3), 2 pages (2014).

International Search Report for PCT/US2022/74139 mailed Oct. 17, 2022, 5 pages.

Kim, K, et al. Structure of a Hallucinogen-Activated Gq-Coupled 5-HT2A Serotonin Receptor. Cell., 182(6):1574-1588 (2020).

National Library of Medicine / National Center for Biotechnology information. Pubchem CIP 10262849, created 2006, modified 2022, 11 pages.

National Library of Medicine / National Center for Biotechnology information. Pubchem CIP 188007, created 2005, modified 2022, 18 pages.

National Library of Medicine / National Center for Biotechnology information. Pubchem CIP 19970992, created 2007, modified 2022, 8 pages.

National Library of Medicine / National Center for Biotechnology information. Pubchem CIP 21615262, created 2007, modified 2022, 9 pages.

(Continued)

*Primary Examiner* — Timothy R Rozof
(74) *Attorney, Agent, or Firm* — Baker, Donelson, Bearman, Caldwell & Berkowitz, PC

(57) ABSTRACT

The invention features indolealkylamine compounds and pharmaceutical compositions useful for treating 5-HT2 responsive conditions. Also provided are methods of using the compounds or compositions of the invention for treating 5-HT2 responsive conditions such as depression or inflammation in a subject in need thereof.

18 Claims, 7 Drawing Sheets

(56) References Cited

OTHER PUBLICATIONS

National Library of Medicine / National Center for Biotechnology information. Pubchem CIP 23640750, created 2008, modified 2022, 12 pages.
National Library of Medicine / National Center for Biotechnology information. Pubchem CIP 2749894, created 2005, modified 2022, 9 pages.
National Library of Medicine / National Center for Biotechnology information. Pubchem CIP 76548340, created 2014, modified 2022, 10 pages.
Schultz, D. M. Synthesis of serotonin agonists as 5-HT-2a and 5-HT-2c receptor molecular probes. Journal of Undergraduate Research IX, 6 pages (2006).
Squire, L. R. et al. (eds.). Fundamentals of Neuroscience. Third Edition, Elsevier (2008).
Stahl, P. H. et al. (eds). Pharmaceutical Salts: Properties, Selection, and Use. Wiley-VCH (2008).
Swarbrick, J. et al. (eds). Encyclopedia of Pharmaceutical Technology. Marcel Dekker, New York (1988), 172 pages.
Swarbrick, J. et al. (eds). Encyclopedia of Pharmaceutical Technology. Marcel Dekker, New York (1988), 163 pages.
World Health Organization (WHO). The ICD-10 Classification of Mental and Behavioral Disorders: Diagnostic Criteria for Research. Geneva: World Health Organization, 262 pages (1993).
Written Opinion for PCT/US2022/74139 mailed Oct. 17, 2022, 8 pages.
Bernard Bourrie (2004) "Sigma receptor ligands: applications in inflammation and oncology" Current Opinions in Investigational Drugs. vol. 5(11):p. 1158-1163.†
M Carmen Ruiz-Cantero (2020) "Sigma-1 receptor: A drug target for the modulation of neuroimmune and neuroglial interactions during chronic pain" Pharmacological Research. Jan.(261):p. 105339.†

* cited by examiner
† cited by third party

Phenethylamines
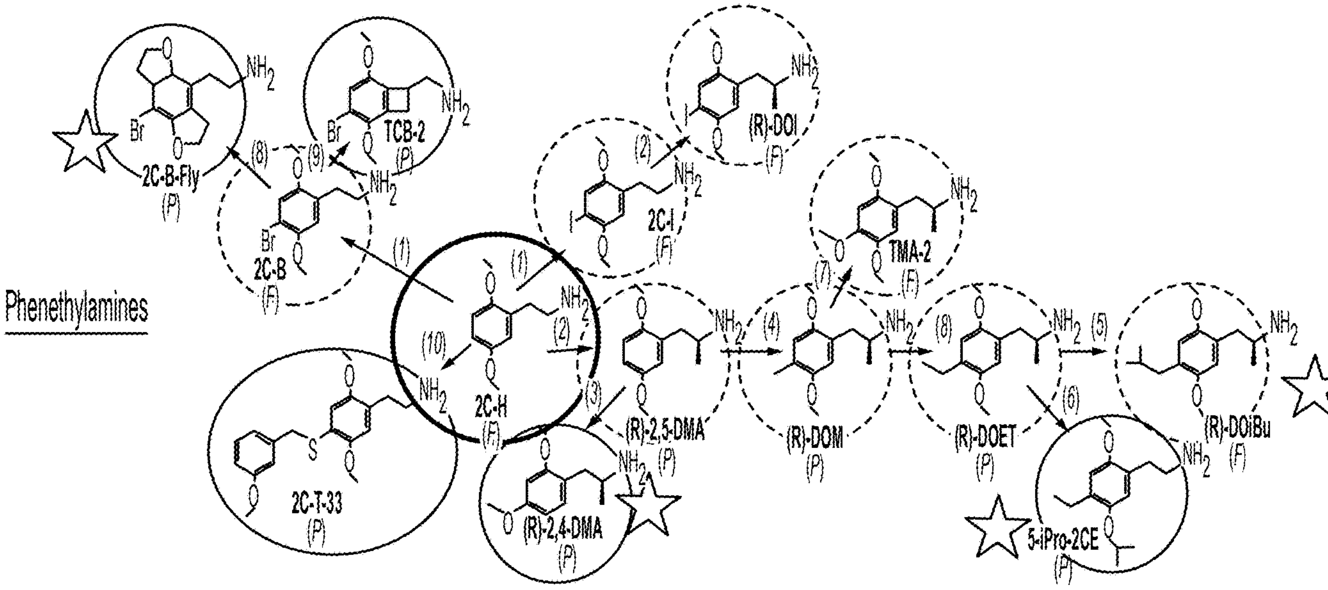
*Allowable*
4 - halogen
Alpha-methyl
4- Aliphatic chain
*Detrimental*
Rigidification of methoxies
Rigidification of side chain
Loss or modification of 5' methoxy
4-thio, or too large a bulk at 4-position
Tryptamines
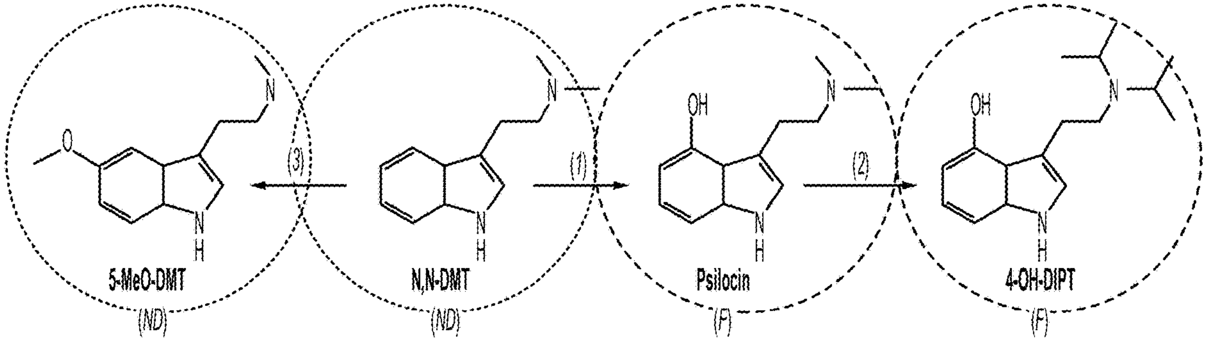
*Allowable*
4-OH
Nature of the N,N-groups
Not allowable
Lack of a "4-OH"
5-Methoxy?
Figure 3

SAR of anti-inflammatory efficacy

Phenethylamines

Tryptamines

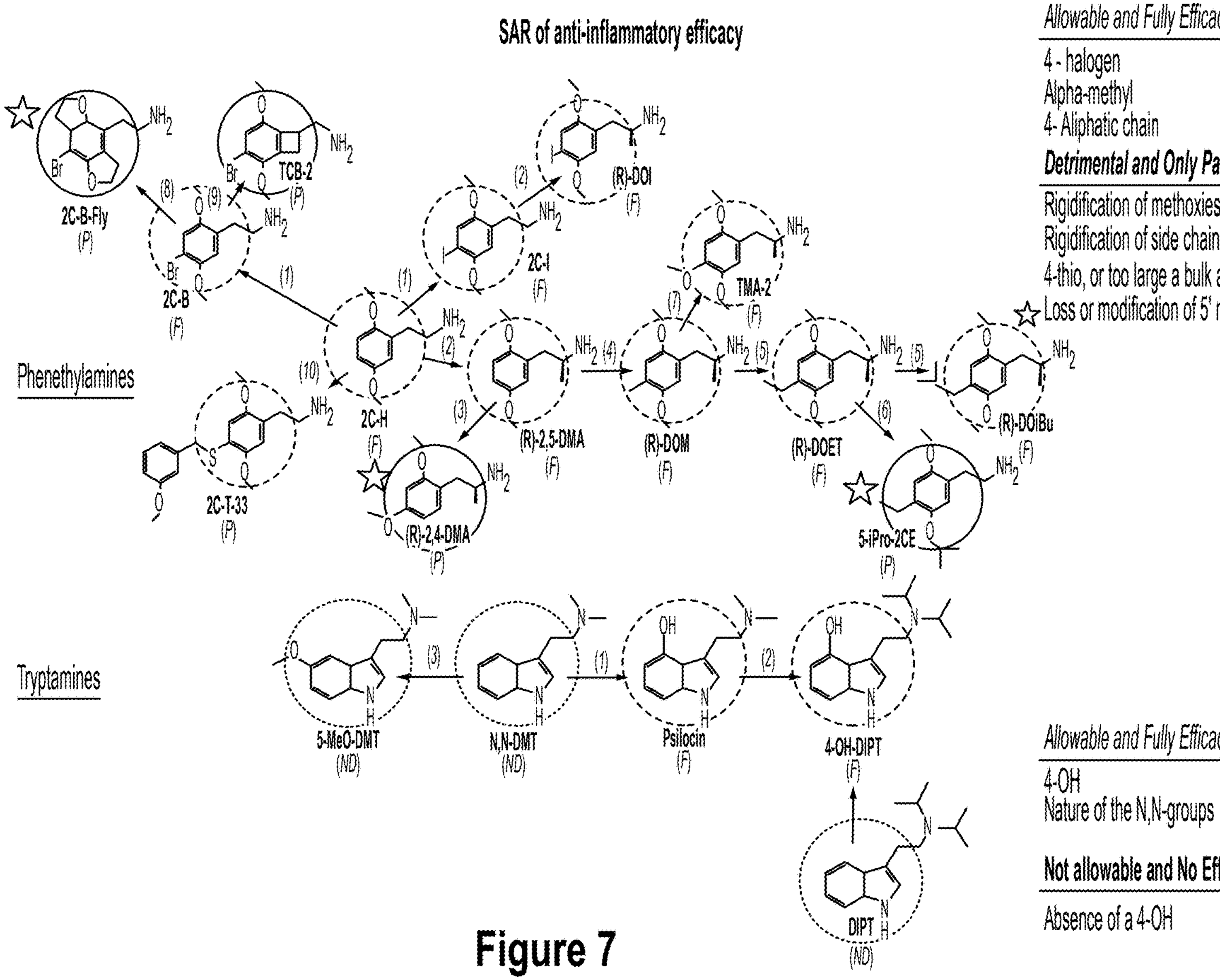

2C-B-Fly (P)
TCB-2 (P)
2C-B (F)
2C-H (F)
2C-I (F)
(R)-DOI (F)
2C-T-33 (P)
(R)-2,4-DMA (P)
(R)-2,5-DMA (F)
(R)-DOM (F)
TMA-2 (F)
(R)-DOET (F)
(R)-DOiBu (F)
5-iPro-2CE (P)
5-MeO-DMT (ND)
N,N-DMT (ND)
Psilocin (F)
4-OH-DIPT (F)
DIPT (ND)

*Allowable and Fully Efficacious (F)*

4 - halogen
Alpha-methyl
4- Aliphatic chain

*Detrimental and Only Partially Efficacious (P)*

Rigidification of methoxies
Rigidification of side chain
4-thio, or too large a bulk at 4-position
Loss or modification of 5' methoxy

*Allowable and Fully Efficacious (F)*

4-OH
Nature of the N,N-groups

Not allowable and No Efficacy (ND)

Absence of a 4-OH

Figure 7

COMPOUNDS AND METHODS FOR TREATING 5-HT2 RESPONSIVE CONDITIONS

The present application is a National Stage Entry of PCT Application No. PCT/US2022/074139, filed on Jul. 26, 2022, which claims priority from US Provisional Paten Application Ser. No. 63/225,755, filed on Jul. 26, 2021, the contents of each of which are incorporated herein by reference in their entireties.

All patents, patent applications and publications cited herein are hereby incorporated by reference in their entireties. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

In general, the invention features compositions and methods for treating 5-HT2 responsive conditions.

BACKGROUND OF THE INVENTION

Significant interest in the therapeutic application of 5-HT2 receptor ligands has developed, based upon evidence of possible therapeutic effects in a wide array of 5-HT2 responsive conditions (e.g., mitigating or improving conditions and disorders via 5-HT2 receptor target modulation), including psychiatric conditions, pain disorders, immunological conditions, and neurological conditions.

There is a need in the field for discovery and development of small molecule 5-HT2 receptor ligands with more desirable therapeutic, absorption, distribution, pharmacokinetic, and/or safety profiles.

SUMMARY OF THE INVENTION

The invention discloses a new class of ligands for the 5-HT2 receptors that have potent pharmacological properties. Also provided are methods of using the compounds or compositions of the invention, e.g., for treating an inflammatory or a neurological disorder in a subject in need thereof.

An aspect of the invention features a compound of formula (I), or a pharmaceutically acceptable salt thereof:

(I)

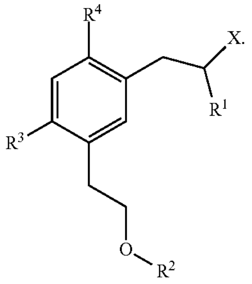

In formula (I), X is $NH_2$, $NH(CH_3)$, $N(CH_3)_2$, or $N(CH_3)_3$; $R^1$ is H or $CH_3$; $R^2$ is H or $CH_3$; $R^3$ is H, halogen, trifluoromethyl, CN, optionally substituted $C_{1-8}$ alkyl, optionally substituted $C_{2-8}$ alkenyl, optionally substituted $C_{1-8}$ alkoxy, and $C_1$-$C_8$ alkylthio; and $R^4$ is H, OH, $OCH_3$, or $OCH_2CH_3$.

In an embodiment of formula (I), $R^3$ is selected from bromo, iodo, CN, $—CH_3$, $—CH_2CH_3$, $—CH(CH_3)_2$, $—CH_2CH(CH_3)_2$, $—CH_2CH_2CH(CH_3)_2$, $—CH_2CH_2CH_2CH_3$, $—C(CH_3)_3$, $—CH_2C(CH_3)_3$; $—OCH(CH_3)_2$, $—OC(CH_3)_3$, and $C_1$-$C_8$ alkylthio, or a group selected from:

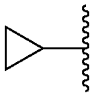
,

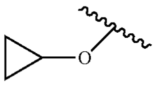
,

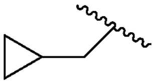
,

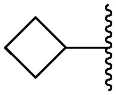
,

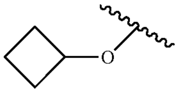
, or

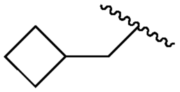
.

In particular embodiments, the compound of formula (I) is selected from any one of compounds 1-4:

(1)

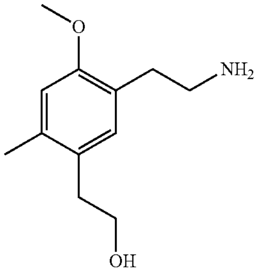

(2)

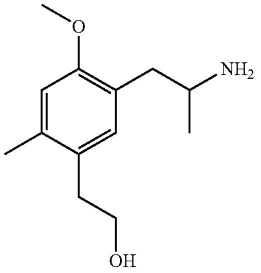

-continued (3)

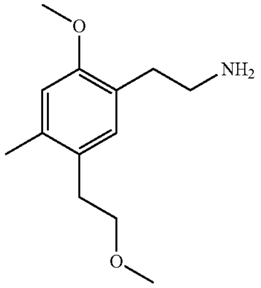

(4)

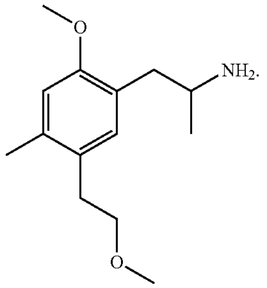

In another aspect, the invention features a compound of formula (II), or a pharmaceutically acceptable salt thereof:

(II)

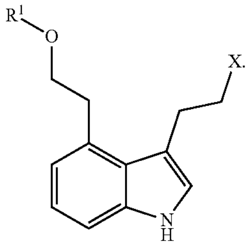

In formula (II), $R^1$ is H or $CH_3$; X is $N(R^2)(R^3)$ or $N(R^2)(R^3)(CH_3)$; and each of $R^2$ and $R^3$ are, independently, selected from $—CH_3$, $—CH_2CH_3$, and $—CH(CH_3)_2$, $—CH_2CH(CH_3)_2$. In particular embodiments, the compound of formula (II) is selected from any one of compounds 5-8:

(5)

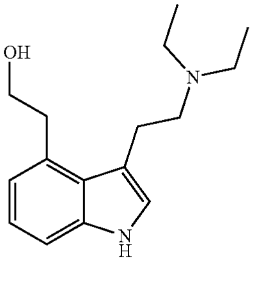

-continued (6)

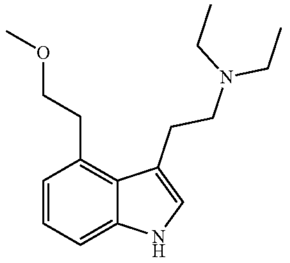

(7)

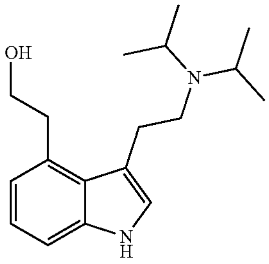

(8)

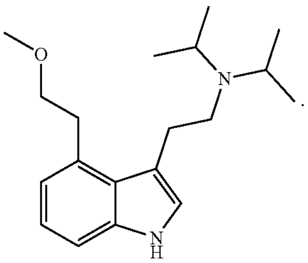

In another aspect, the invention includes a composition of any of the preceding aspects (e.g., a compound of formulas (I) or (II), or a pharmaceutically acceptable salt thereof), and a pharmaceutically acceptable excipient. Such a pharmaceutical composition can be formulated, e.g., for oral, intranasal, subcutaneous, intramuscular, parenteral, topical, intraocular or pulmonary administration.

In another aspect, provided herein is a method of treating 5-HT2 responsive conditions in a subject in need thereof, the method including administering to the subject a therapeutically effective amount of the compound or the pharmaceutical composition of any of the preceding aspects. In particular embodiments the 5-HT2 responsive condition is an inflammatory or neurological disorder.

In some embodiments of any of the preceding embodiments or any of the methods described herein, the 5-HT2 responsive condition is an inflammatory disorder selected from asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, conjunctivitis, Alzheimer's disease, or any inflammatory condition described herein.

In another aspect, provided herein is a method of treating a psychological condition in a subject in need thereof, the method including administering to the subject a therapeutically effective amount of the compound or the pharmaceutical composition of any of the preceding aspects. In particular embodiments, the psychological condition is depression, anxiety, addiction, post-traumatic stress disorder, an eating disorder, compulsive behavior, autism spectrum disorders, or any psychological condition described herein.

In another aspect, provided herein is a method of treating chronic pain in a subject in need thereof, the method including administering to the subject a therapeutically effective amount of the compound or the pharmaceutical composition of any of the preceding aspects.

In another aspect, the described composition of matter embodies a new chemotype class of ligands targeting the 5-HT2 receptors that offers structural differentiation from previously known chemotype ligand classes for these receptors, namely substituted phenethylamines, lysergamides, and tryptamines non exhaustively. A different structural chemotype will likely not replicate the extended pharmacology at secondary and complementary targets known for these other ligand classes. Thus, any additional activities at secondary metabotropic, ionotropic, transporter, or enzyme targets for the molecules described in this application could contribute to an overall distinctive pharmacological profile compared to existing 5-HT2 receptor targeting medicines.

In any of the methods provided herein, the compound can be administered by any suitable route of administration, e.g., orally, intranasally, or by inhalation. In some embodiments, the present compound or pharmaceutical composition thereof is administered by one or more of a variety of routes, including nasal, buccal, oral, by inhalation (e.g., as an oral spray, nebulizer, nasal spray, or aerosol), intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, enteral, vitreal, intratumoral, sublingual; by intratracheal instillation, bronchial instillation, and/or through a portal vein catheter. In some embodiments the composition is administered by systemic intravenous injection. In specific embodiments the composition is administered intravenously and/or orally.

BRIEF DESCRIPTION OF THE FIGURES

FIG. 3 shows structure-activity relationship results. The loss or modification of the 5-methoxy results in reduced efficacy in DOx/2Cx compounds. The lack of 4-OH in tryptamine results in a complete loss of efficacy for anti-inflammatory effects (e.g. psilocin vs N,N-DMT).

FIG. 7 shows structure-activity relationship results. These results show the importance of the 4-OH group on tryptamines for anti-inflammatory activity.

DEFINITIONS

Figure 1:
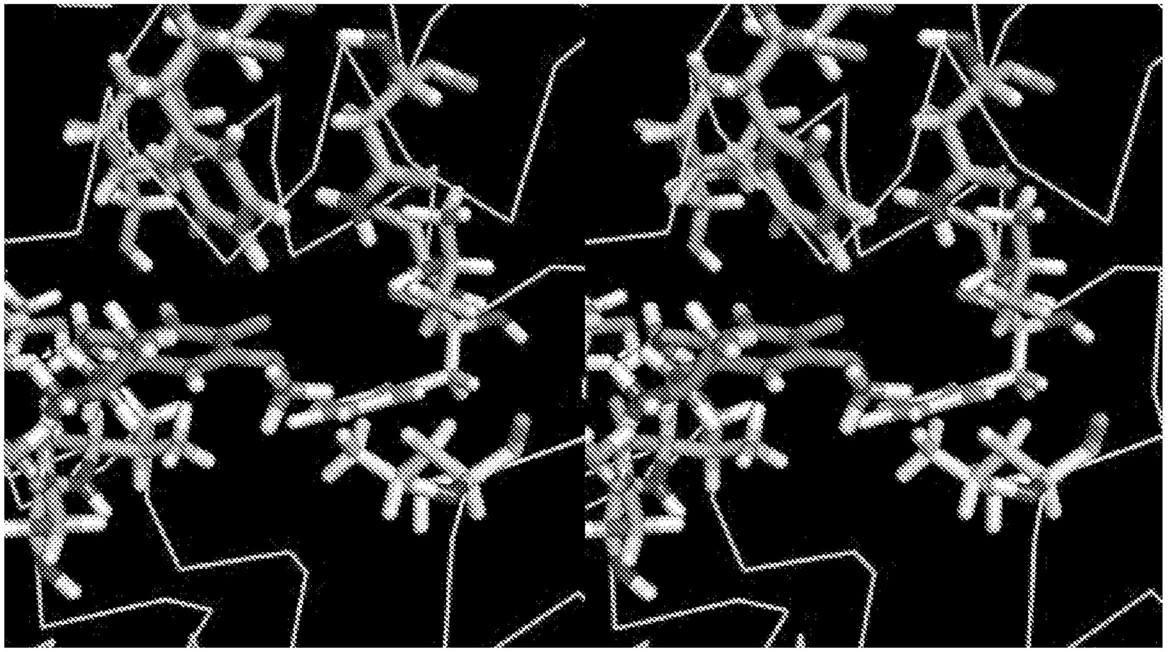
FIG. 1 shows an in silico diagram of the aromatic ring of a DOx compound (dark blue; DOI in this example) positioned according to the recently published structure of 25CN—NBOH in the binding pocket of the human 5-HT2A receptor. Note that there is nothing but an empty space for the 5-MeO to poke into.

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

The singular forms “a”, “an” and “the” include plural reference unless the context clearly dictates otherwise. The use of the word “a” or “an” when used in conjunction with the term “comprising” in the claims and/or the specification can mean “one,” but it is also consistent with the meaning of “one or more,” “at least one,” and “one or more than one.”

Wherever any of the phrases “for example,” “such as,” “including” and the like are used herein, the phrase “and without limitation” is understood to follow unless explicitly stated otherwise. Similarly, “an example,” “exemplary” and the like are understood to be nonlimiting.

The term “substantially” allows for deviations from the descriptor that do not negatively impact the intended purpose. Descriptive terms are understood to be modified by the term “substantially” even if the word “substantially” is not explicitly recited.

The terms “comprising” and “including” and “having” and “involving” (and similarly “comprises”, “includes,” “has,” and “involves”) and the like are used interchangeably and have the same meaning. Specifically, each of the terms is defined consistent with the common United States patent law definition of “comprising” and is therefore interpreted to be an open term meaning “at least the following,” and is also interpreted not to exclude additional features, limitations, aspects, etc. Thus, for example, “a process involving steps a, b, and c” means that the process includes at least steps a, b and c. Wherever the terms “a” or “an” are used, “one or more” is understood, unless such interpretation is nonsensical in context.

As used herein the term “about” is used herein to mean approximately, roughly, around, or in the region of. When the term “about” is used in conjunction with a numerical range, it modifies that range by extending the boundaries above and below the numerical values set forth. In general, the term “about” is used herein to modify a numerical value above and below the stated value by a variance of 20 percent up or down (higher or lower).

At various places in the present specification, substituents of compounds of the present disclosure are disclosed in groups or in ranges. Itis specifically intended that the present disclosure include each and every individual subcombination of the members of such groups and ranges. For example, the term “$C_{1-8}$ alkyl” is specifically intended to individually disclose methyl, ethyl, $C_3$ alkyl, $C_4$ alkyl, $C_5$ alkyl, $C_6$ alkyl, $C_7$ alkyl, and $C_8$ alkyl. Herein a phrase of the form "optionally substituted X" (e.g., optionally substituted alkyl) is intended to be equivalent to "X, wherein X is optionally substituted" (e.g., "alkyl, wherein the alkyl is optionally substituted"). Itis not intended to mean that the feature "X" (e.g., alkyl) per se is optional.

As used herein, the terms "alkyl" and the prefix "alk-" are inclusive of both straight chain and branched chain groups and of cyclic groups, i.e., cycloalkyl, and combinations thereof. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-8}$ alkyl group can be substituted or unsubstituted. Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, $C_{2-7}$ heterocyclyl, quaternary amino, hydroxyalkyl, carboxyalkyl, and carboxyl groups. $C_{1-8}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

"$C_{2-8}$ alkenyl" refers to a branched or unbranched hydrocarbon group containing one or more double bonds and having from 2 to 8 carbon atoms. A $C_{2-8}$ alkenyl can include monocyclic or polycyclic rings, in which each ring can have from three to six members. The $C_{2-8}$ alkenyl group can be substituted or unsubstituted. Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. $C_{2-8}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl. In particular embodiments the $C_{2-8}$ alkenyl has a cis configuration around the double bond.

"$C_{2-7}$ heterocyclyl" refers to a stable 5- to 7-membered monocyclic or 7- to 14-membered bicyclic heterocyclic ring which is saturated, partially unsaturated, or unsaturated (aromatic), and which comprises 2 to 7 carbon atoms and 1, 2, 3, or 4 heteroatoms independently selected from the group consisting of N, O, and S, and including any bicyclic group in which any of the above-defined heterocyclic rings is fused to a benzene ring. The heterocyclyl group can be substituted or unsubstituted. Exemplary substituents include alkoxy, aryloxy, sulfhydryl, alkylthio, arylthio, halide, hydroxy, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. The nitrogen and sulfur heteroatoms can be oxidized. The heterocyclic ring can be covalently attached via any heteroatom or carbon atom which results in a stable structure, e.g., an imidazolinyl ring can be linked at either of the ring-carbon atom positions or at the nitrogen atom. A nitrogen atom in the heterocycle can be quaternized. For example, when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, beta-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

"$C_{6-12}$ aryl" refers to an aromatic group having a ring system comprised of carbon atoms with conjugated $\pi$ electrons (e.g., phenyl). The aryl group has from 6 to 12 carbon atoms. Aryl groups can comprise monocyclic, bicyclic, or tricyclic rings, in which each ring can comprise five or six members. The aryl group can be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

"$C_{7-14}$ alkaryl" refers to an alkyl substituted by an aryl group (e.g., benzyl, phenethyl, or 3,4-dichlorophenethyl) having from 7 to 14 carbon atoms.

"$C_{3-10}$ alkheterocyclyl" refers to an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

"$C_{1-8}$ heteroalkyl" refers to a branched or unbranched alkyl, alkenyl, or alkynyl group having from 1 to 8 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl can comprise monocyclic, bicyclic, or tricyclic rings, in which each ring can comprise three to six members. The heteroalkyl group can be substituted or unsubstituted. Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, quaternary amino, $C_{2-7}$ heterocyclyl, hydroxyalkyl, hydroxyalkyl, carboxyalkyl, and carboxyl groups. Examples of $C_{1-8}$ heteroalkyls include, without limitation, methoxymethyl and ethoxyethyl.

"Halide" refers to bromine, chlorine, iodine, or fluorine.

"Fluoroalkyl" refers to an alkyl group that is substituted with one or more fluorine atoms.

"Carboxyalkyl" refers to a chemical moiety with the formula —(R)—COOH, wherein R is selected from $C_{1-8}$ alkyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

"Hydroxyalkyl" refers to a chemical moiety with the formula —(R)—OH, wherein R is selected from $C_{1-8}$ alkyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

"Alkoxy" refers to a chemical substituent of the formula —OR, wherein R is selected from $C_{1-8}$ alkyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

"Aryloxy" refers to a chemical substituent of the formula —OR, wherein R is a $C_{6-12}$ aryl group.

"Alkylthio" can refer to a chemical substituent of the formula —SR, wherein R is selected from $C_{1-8}$ alkyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

"Arylthio" refers to a chemical substituent of the formula —SR, wherein R is a $C_{6-12}$ aryl group.

"quaternary amino" refers to a chemical substituent of the formula —(R)—N(R') (R") (R"')$^+$, wherein R, R', R", and R"' are each independently an alkyl, alkenyl, alkynyl, or aryl group. R can comprise an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

"Acyl" refers to a chemical moiety with the formula R—C(O)—, wherein R is selected from $C_{1-8}$ alkyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

Terms such as "a", "an," and "the" are not intended to refer to only a singular entity but include the general class of which a specific example can be used for illustration.

As used herein, the terms "acute stress disorder" and "ASD" refer to a condition that arises as a response to a stressful event or situation of an exceptionally threatening or catastrophic nature, which is likely to cause pervasive distress in an individual (e.g., natural or man-made disaster, combat, serious accident, witnessing the violent death of others, or being the victim of torture, terrorism, rape, or other crime). Like PTSD, acute stress disorder is an anxiety disorder that involves a very specific reaction following exposure to a traumatic event or stressor. However, the duration of acute stress disorder is shorter than that for PTSD, such that the symptoms are present for at least one, two, or three days, but no more than four, five, or six weeks. For individuals exhibiting symptoms persisting for a longer period of time, a diagnosis of PTSD can be warranted.

The term "administration" or "administering" refers to a method of giving a dosage of a compound or pharmaceutical composition to a subject.

By "dysthymia" or "dysthymic disorder" refer to a chronically depressed mood that occurs for most of the day, more days than not, for at least two years. In children and adolescents, the mood can be irritable rather than depressed, and the required minimum duration is one year. During the two-year period (one year for children or adolescents), any symptom-free intervals last no longer than 2 months. During periods of depressed mood, at least two of the following additional symptoms are present: poor appetite or overeating, insomnia or hypersomnia, low energy or fatigue, low self-esteem, poor concentration, or difficulty making decisions, and feelings of hopelessness. The symptoms can cause clinically significant distress or impairment in social, occupational (or academic), or other important areas of functioning. The diagnosis of dysthymia is not made if: the individual has ever had a manic episode, a mixed episode, a hypomanic episode; has ever met the criteria for a cyclothymic disorder; the depressive symptoms occur exclusively during the course of a chronic psychotic disorder (e.g., schizophrenia); or if the disturbance is due to the direct physiological effects of a substance or a general medical condition. After the initial two-years of dysthymic disorder, major depressive episodes can be superimposed on the dysthymic disorder ("double depression"). Diagnostic and Statistical Manual of Mental Disorders (OSM IV), American Psychiatric Press, 4th Edition, I 994. Diagnostic guidance for psychological disorders can be found, for example, in the ICD-10 (The ICD-10 Classification of Mental and Behavioral Disorders: Diagnostic Criteria for Research, Geneva: World Health Organization, 1993) and the DSM-V (American Psychiatric Association. Diagnostic and Statistical Manual of Mental Disorders, Fifth Edition (DSM-V) Arlington, VA.; American Psychiatric Association, 2013).

As used herein, the term "generalized anxiety disorder" refers to conditions characterized by excessive anxiety and worry (i.e., apprehensive expectation). For example, the excessive anxiety and worry occur on more days than not for a period of time (e.g., one, two, three, or four months or more). The anxiety and worry can be associated with (i) restlessness, feeling keyed up, or on edge; and/or (ii) muscle tension. The anxiety and worry can be associated with (a) a marked avoidance of situations in which a negative outcome could occur; (b) a marked time and effort preparing for situations in which a negative outcome could occur; (c) a marked procrastination in behavior or decision-making due to worries; and (d) repeatedly seeking reassurance due to worries. The anxiety, worry, or physical symptoms can cause clinically significant distress or impairment in social, occupational, or other important areas of functioning in many, but not necessarily all individuals with GAD.

As used herein, the terms "obsessive compulsive disorder," "OCD," and "anxiety and obsessive-compulsive spectrum disorders" refer to a condition characterized by obsessions and/or compulsions. Obsessions are recurrent and persistent thoughts, urges, or images that are experienced, at some time during the disturbance, as intrusive and unwanted and that usually cause marked anxiety or distress in which the obsessed individual attempts to ignore or suppress such thoughts, urges, or images, or to neutralize them with some other thought or action (i.e., by performing a compulsion). Compulsions are repetitive behaviors (e.g., hand washing, ordering checking) or mental acts (e.g., praying, counting, repeating words silently) that the person feels driven to perform in response to an obsession, or according to rules that must be applied rigidly. The behaviors or mental acts are aimed at preventing or reducing anxiety or distress, or preventing some dreaded event or situation; however, these behaviors or mental acts either are not connected in a realistic way with what they are designed to neutralize or prevent, or are clearly excessive. Typically the obsessions or compulsions are time consuming (for example, take more than 1 hour a day), or cause clinically significant distress or impairment in social, occupational, or other important areas of functioning.

As used herein, the term "pharmaceutically acceptable salt" refers to those salts of the compounds described herein that are suitable for pharmaceutical use. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately, e.g., by reacting the free base of the compound with a suitable organic acid or inorganic acid, or by reacting the free acid of the compound with a suitable organic acid or inorganic base.

As used herein, the term "panic disorder" refers to a condition characterized by recurrent and unexpected panic attacks. Panic disorder includes both panic disorder with agoraphobia and panic disorder without agoraphobia. Subjects with this condition can exhibit one or both of the following: (i) a persistent concern or worry about additional panic attacks or their consequences (e.g., losing control, having a heart attack, going crazy); and/or (ii) significant maladaptive change in behavior related to the attacks (e.g., behaviors designed to avoid having panic attacks), which can include agoraphobic avoidance.

As used herein, the terms "post traumatic stress disorder" and "PTSD" refer to a condition that arises as a delayed and/or protracted response to a stressful event or situation (either short- or long-lasting) of an exceptionally threatening or catastrophic nature, which can cause pervasive distress in an individual (e.g., natural or man-made disaster, combat, serious accident, witnessing the violent death of others, or being the victim of torture, terrorism, rape, or other crime). Predisposing factors such as personality traits (e.g., compulsive, asthenic) or previous history of neurotic illness can lower the threshold for the development of the condition or aggravate its course, but they are neither necessary nor sufficient to explain its occurrence. PTSD is a less frequent and more enduring consequence of psychological trauma than the more frequently seen acute stress response. PTSD has been recognized in the past as railway spine, stress syndrome, shell shock, battle fatigue, traumatic war neurosis, and post-traumatic stress syndrome. Diagnostic symptoms include re-experiencing original trauma(s), by means of flashbacks or nightmares; avoidance of stimuli associated with the trauma; and increased arousal, such as difficulty falling or staying asleep, anger, and hypervigilance. Formal diagnostic criteria (DSM-V, DSM-IV, and/or ICD-9) require that the symptoms last more than one month and cause significant impairment in social, occupational, or other important areas of functioning (e.g., problems with work and/or relationships). Formal diagnostic criteria can include: (i) intrusion symptoms that are associated with the traumatic event (e.g., (a) spontaneous or cued recurrent, involuntary, and intrusive distressing memories of the traumatic event; (b) recurrent distressing dreams in which the content and/or affect of the dream is related to the event; (c) dissociative reactions (e.g., flashbacks) in which the individual feels or acts as if the traumatic event were recurring (such reactions can occur on a continuum, with the most extreme expression being a complete loss of awareness of present surroundings; (d) intense or prolonged psychological distress at exposure to internal or external cues that symbolize or resemble an aspect of the traumatic event; and/or (e) marked physiological reactions to reminders of the traumatic event); (ii) persistent avoidance of stimuli associated with the traumatic event (e.g., (a) thoughts, feelings, or physical sensations that arouse recollections of the traumatic event; (b) activities, places, physical reminders, or times (e.g., anniversary reactions) that arouse recollections of the traumatic event; and/or (c) people, conversations, or interpersonal situations that arouse recollections of the traumatic event); (iii) negative alterations in cognitions and mood that are associated with the traumatic event (e.g., (a) inability to remember an important aspect of the traumatic event (typically dissociative amnesia); (b) persistent and exaggerated negative expectations about one's self, others, or the world; (c) persistent distorted blame of self or others about the cause or consequences of the traumatic event; (d) pervasive negative emotional state (e.g., fear, horror, anger, guilt, or shame); (e) markedly diminished interest or participation in significant activities; (f) feeling of detachment or estrangement from others; and/or (g) persistent inability to experience positive emotions (e.g., unable to have loving feelings, psychic numbing); and (iv) alterations in arousal (i.e., hyperarousal) and reactivity that are associated with the traumatic event (e.g., (a) irritable, angry, or aggressive behavior; (b) reckless or self-destructive behavior; (c) hypervigilance; (d) exaggerated startle response; (e) problems with concentration; and/or (f) sleep disturbance (e.g., difficulty falling or staying asleep, or restless sleep)). Formal diagnostic criteria can further include that the duration of disturbance is more than a certain period of time (e.g., one month, three months, or six months) and that the disturbance causes clinically significant distress or impairment in social, occupational, or other important areas of functioning. In a small proportion of patients the condition can show a chronic course over many years and a transition to an enduring personality change. The three main symptoms associated with PTSD are (1) "reliving" the traumatic event, such as flashbacks, nightmares, intrusive thoughts and recollections, (2) avoidance behaviors and emotional numbing, and (3) hypersensitivity such as an inability to sleep, anxious feelings, overactive startle response, hyperarousal, hypervigilance, irritability, and outbursts of anger.

As used herein, the terms "psychological disorder" and "psychological condition" refer to a condition characterized by a disturbance in one's emotional or behavioral regulation that reflects a dysfunction in the psychological, biological, or developmental processes underlying mental function. Psychological disorders include, but are not limited to depressive disorders (major depression, treatment resistant depression, melancholic depression, atypical depression, or dysthymia), anxiety disorders (end of life anxiety, generalized anxiety disorder, panic disorder, social anxiety, post-traumatic stress disorder, acute stress disorder, obsessive compulsive disorder, or social phobia), addictions (e.g., substance abuse, e.g., alcoholism, tobacco abuse, or drug abuse)), eating disorders (e.g., anorexia nervosa, bulimia nervosa, and binge eating disorder) and compulsive behavior disorders (e.g., primary impulse-control disorders or obsessive-compulsive disorder). Psychological disorders can be any psychological condition associated with one or more symptoms, e.g., somatic symptoms (e.g., chronic pain, anxiety disproportionate to severity of physical complaints, pain disorder, body dysmorphia, conversion (i.e., loss of bodily function due to anxiety), hysteria, or neurological conditions without identifiable cause), or psychosomatic symptoms (e.g., back pain, fibromyalgia, migraines, and chronic fatigue syndrome). Psychological disorders also include repetitive body-focused behaviors, such as tic disorders (e.g., Tourette's Syndrome, trichotillomania, nail-biting, temporomandibular disorder, thumb-sucking repetitive oral-digital, lip-biting, fingernail biting, eye-rubbing, skin-picking, or a chronic motor tic disorder). In some cases, development of a psychological disorder is associated with or characterized by a prodromal symptom, such as depressed mood, decreased appetite, weight loss, increased appetite, weight gain, initial insomnia, middle insomnia, early waking, hypersomnia, decreased energy, decreased interest or pleasure, self-blame, decreased concentration, indecision, suicidality, psychomotor agitation, psychomotor retardation, crying more frequently, inability to cry, hopelessness, worrying/brooding, decreased self-esteem, irritability, dependency, self-pity, somatic complaints, decreased effectiveness, helplessness, and decreased initiation of voluntary responses.

As used herein, the terms "social phobia" and "social anxiety disorder" refer to a condition characterized by fear or anxiety associated with one or more social situations. Subjects with this condition typically exhibit a marked fear or anxiety about one or more social situations in which the person is exposed to possible scrutiny by others. Examples include social interactions (e.g., having a conversation), being observed (e.g., eating or drinking), or performance in front of others (e.g., giving a speech). For example, an individual with this condition (i) fears that he or she will act in a way, or show anxiety symptoms that will be negatively evaluated (i.e., be humiliating embarrassing, lead to rejection, or offend others); (ii) the social situations almost invariably provoke immediate fear or anxiety; (iii) the social situations are avoided or endured with intense fear or anxiety; and (iv) the fear or anxiety is out of proportion to the danger posed by the social situation. In children, the fear or anxiety can be expressed by crying, tantrums, freezing, clinging shrinking or refusal to speak in social situations. The fear, anxiety, and avoidance can cause clinically significant distress or impairment in social, occupational, or other important areas of functioning.

The term "therapeutically effective amount," as used herein, refers to an amount, e.g., pharmaceutical dose, effective in inducing a desired effect in a subject or in treating a subject having a condition or disorder described herein (e.g., an inflammatory disorder). Itis also to be understood herein that a "therapeutically effective amount" can be interpreted as an amount giving a desired therapeutic and/or preventative effect, taken in one or more doses or in any dosage or route, and/or taken alone or in combination with other therapeutic agents. For example, in the context of administering a composition described herein that is used for the treatment of a disorder or condition, an effective amount of a compound is, for example, an amount sufficient to prevent, slow down, or reverse the progression of the disorder or condition as compared to the response obtained without administration of the compound.

As used herein, the terms "treat," "treating," or "treatment" refer to administration of a compound or pharmaceutical composition for a therapeutic purpose. To "treat a disorder" or use for "therapeutic treatment" refers to administering treatment to a patient already suffering from a disease to ameliorate the disease or one or more symptoms thereof to improve the patient's condition (e.g., by reducing one or more symptoms of a 5-HT2 responsive condition, such as inflammation, depression, anxiety, Alzheimer's disease, etc.). The term "therapeutic" includes the effect of mitigating deleterious clinical effects of certain inflammatory processes (i.e., consequences of the inflammation, rather than the symptoms of inflammation). The methods of the invention can be used as a primary prevention measure, i.e., to prevent a condition or to reduce the risk of developing a condition. Prevention refers to prophylactic treatment of a patient who may not have fully developed a condition or disorder, but who is susceptible to, or otherwise at risk of, the condition. Thus, in the claims and embodiments, the methods of the invention can be used either for therapeutic or prophylactic purposes.

By "unipolar depression" or "major depressive disorder" refer to a clinical course that is characterized by one or more major depressive episodes in an individual without a history of manic, mixed, or hypomanic episodes. The diagnosis of unipolar depression is not made if: manic, mixed, or hypomanic episodes develop during the course of depression; if the depression is due to the direct physiological effects of a substance; if the depression is due to the direct physiological effects of a general medical condition; if the depression is due to a bereavement or other significant loss ("reactive depression"); or if the episodes are better accounted for by schizoaffective disorder and are not superimposed on schizophrenia, schizophreniform disorder, delusional disorder, or psychotic disorder. If manic, mixed, or hypomanic episodes develop, then the diagnosis is changed to a bipolar disorder. Depression can be associated with chronic general medical conditions (e.g, diabetes, myocardial infarction, carcinoma, and stroke). For example, unipolar depression can be more severe than dysthymia. The essential feature of a major depressive episode is a period of at least two 15 weeks during which there is either depressed mood or loss of interest or pleasure in nearly all activities. In children and adolescents, the mood can be irritable rather than sad. The episode can be a single episode or can be recurrent. The individual also experiences at least four additional symptoms drawn from a list that includes changes in appetite or weight, sleep, and psychomotor activity; decreased energy; feelings of worthlessness or guilt; difficulty thinking concentrating, or making decisions; or recurrent thoughts of death or suicidal ideation, plans, or attempts. Each symptom must be newly present or must have clearly worsened compared with the person's pre-episode status. The symptoms must persist for most of the day, nearly every day, for at least two consecutive weeks, and the episode must be accompanied by clinically significant distress or impairment in social, occupational (or academic), or other important areas of functioning (Diagnostic and Statistical Manual of Mental Disorders (OSM IV), American Psychiatric Press, 4th Edition, 1994). Diagnostic guidance for psychological disorders can be found, for example, in the ICD-10 (The ICD-10 Classification of Mental and Behavioral Disorders: Diagnostic Criteria for Research, Geneva: World Health Organization, 1993) and the DSM-V (American Psychiatric Association. Diagnostic and Statistical Manual of Mental Disorders, Fifth Edition (DSM-V) Arlington, VA.; American Psychiatric Association, 2013).

Other features and advantages of the invention will be apparent from the following Detailed Description, Examples, and Claims.

DETAILED DESCRIPTION OF THE INVENTION

Aspects of the invention are drawn towards compounds and methods of treating 5-HT2 responsive conditions. The invention comprises compounds of formulas (I) and (II). The compounds can be useful for treating 5-HT2 responsive conditions (e.g., inflammation, pain, depression, anxiety, PTSD, and Alzheimer's disease). The compounds were designed (via in silico modelling) to engage certain amino acid residues in the orthosteric binding pocket of 5-HT2A. The compounds of the invention can have improved potencies and/or efficacies for anti-inflammatory effects in the native 5-HT2A receptor relative to other 5-HT2A ligands.

Detailed descriptions of one or more embodiments are provided herein. It is to be understood, however, that the invention can be embodied in various forms. Therefore, specific details disclosed herein are not to be interpreted as limiting, but rather as a basis for the claims and as a representative basis for teaching one skilled in the art to employ the present invention in any appropriate manner.

5-HT2 Receptor

Serotonin (5-hydroxytryptamine; 5-HT) is a neurotransmitter derived from the amino acid, tryptophan which appears to play roles in mood, emotional behavior, and sleep (Bear, Connors, and Paradiso, Neuroscience Exploring the Brain, Wolter Kluwer, 2016). Although serotonin was initially identified and isolated from peripheral tissues, its potential involvement in psychiatric disorders has been the subject of research (Squire, L. R., Bloom, F. E., Spitzer, N. C., de Luc, S., Gosh, A., Berg, D., (Eds.), Fundamentals of Neuroscience, Third Edition, Elsevier, 2008). The effects of 5-HT are mediated through interactions at seven different families of receptor proteins (5-HT receptors), comprised of 14 different subtypes, consisting of 13 G-protein coupled receptors and one ligand-gated ion channel. For example, $5\text{-HT}_{1A}$, $5\text{-HT}_{1B}$, $5\text{-HT}_{1D}$, $5\text{-HT}_{1E}$, $5\text{-HT}_{2A}$, $5\text{-HT}_{2B}$, $5\text{-HT}_{4}$, and $5\text{-HT}_{5A}$ are G-protein-coupled neurotransmitter receptors for 5-HT (*Bear* et al. 2016), has been identified in eliciting psychedelic effects in humans.

Aspects of the invention are drawn towards compounds that can engage certain amino acid residues in the orthosteric binding pocket of 5-HT2A to elicit anti-inflammatory and/or anti-ROS effects in a subject. As used herein, the term "engage" can refer to non-covalent interactions between molecules which leads to association, interactions, and/or binding between the molecules. For example, the non-covalent interaction comprises hydrogen bonding, ionic forces, and van der Waals forces. For example, the compound engages certain residues of transmembrane helices. For example, the compound engages certain amino acid residues in transmembrane helix 6 (TM6). For example, the compound engages an asparagine residue on TM6. For example, the compound engages an amino acid residue at position 343 of TM6. For example, the compound engages position 343 of TM6 via hydrogen bonding.

As used herein, h5-HT2A can be used interchangeably with 5-HT2A. As used herein, h5-HT2A can refer to human 5-HT2A.

Compounds

Aspects of the invention are drawn to compounds which engage certain aminoacid residues of 5-HT2A. In embodiments, compounds of the invention can engage asparagine 343 (N343) of TM6 in 5-HT2A directly. For example, compounds of the invention do not require an intermediate compound (e.g. structural water) to engage N343 of TM6 in 5-HT2A. For example, compounds of the invention can hydrogen bond directly with N343 of TM6 of 5-HT2A.

Without wishing to be bound by theory, 2-methoxyethyl containing compounds can directly engage N343 of TM6 in 5-HT2A. Without wishing to be bound by theory, compounds (including, but not limited to, DOx and 2Cx compounds) containing and/or modified to contain 2-methoxyethyl groups can directly engage N343 of TM6 of 5-HT2A. In embodiments, compounds of the invention can contain a 5-methoxyethyl group. In embodiments, the 5-methoxyethyl group can directly engage N343 of TM6 of 5-HT2A. For example, Dox/2Cx compounds with a 5-methoxyethyl group can directly engage N343 of 5-HT2A. In embodiments, compounds of the invention can contain a 5-methoxy group. In embodiments, the 5-methoxy group can directly engage N343 of TM6 of 5-HT2A. For example, DOx/2Cx compounds with a 5-methoxy group can directly engage N343 of 5-HT2A. Without wishing to be bound by theory, the 5-methoxy can be replaced by a 5-(2-hydroxyethyl). Without wishing to be bound by theory, replacing a 5-methoxy with a 5-(2-hydroxyethyl) can decrease blood-brain barrier penetration. Without wishing to be bound by theory, decreasing blood-brain barrier penetration can reduce behavioral liability.

Without wishing to be bound by theory, compounds (including, but not limited to, tryptamines) containing and/or modified to contain 4-hydroxy can directly engage N343 of TM6 of 5-HT2A. Without wishing to be bound by theory, replacing the 4-hydroxy group on a compound (e.g. a tryptamine compound) with 4-(2-hydroxyethyl) or 4-(2-methoxyethyl) can provide improved selectivity for 5-HT2 over 5-HT1A receptor.

The invention features compounds of formulas (I) and (II):

(I)

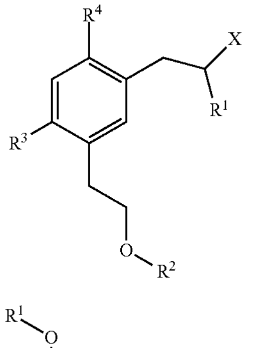

(II)

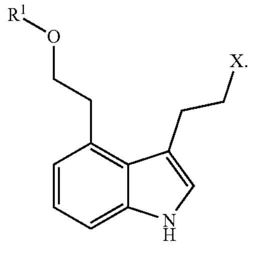

and pharmaceutically acceptable salts thereof.

The compounds of formula (I) can be synthesized using methods analogous to those described in Scheme 1 (below).

Scheme 1

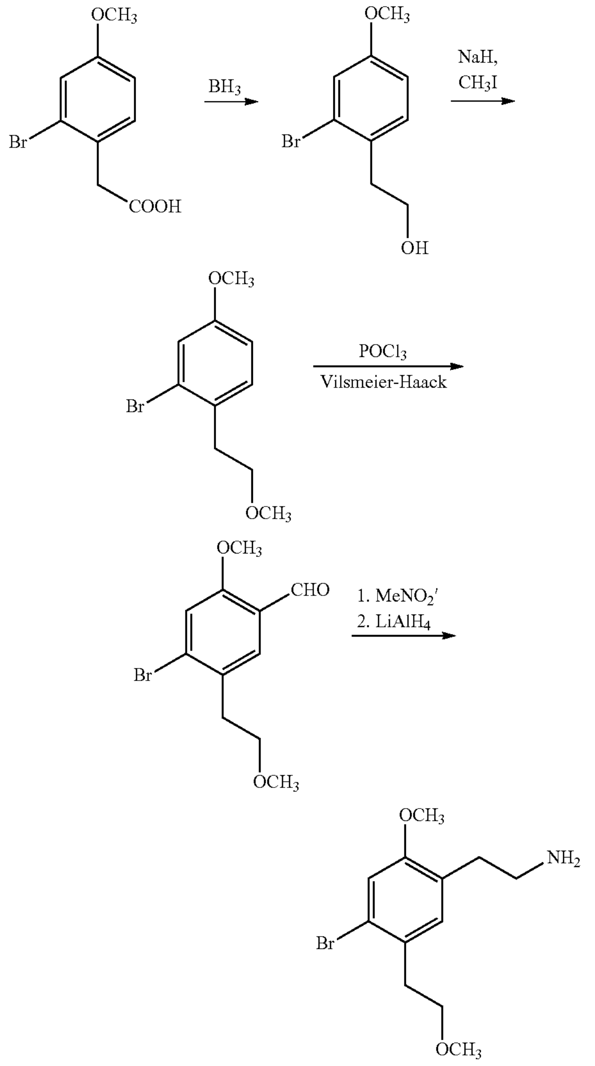

The compounds of formula (II) can be synthesized using methods analogous to those described in Scheme 2 (below).

Scheme 2

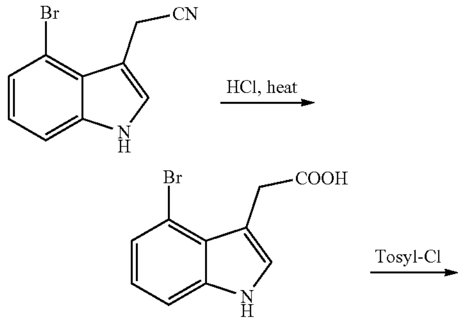

-continued

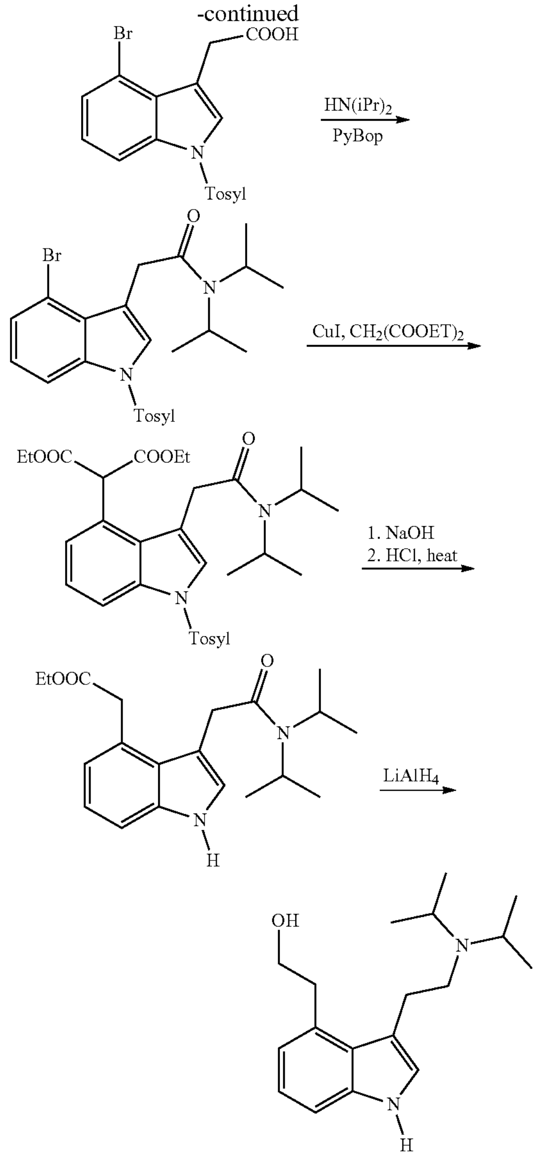

Without wishing to be bound by theory, compounds described herein can be quaterinzed to produced desired selectivity for therapeutic targets. Without wishing to be bound by theory, compounds described herein can be quaternized to peripherally restrict them. For example, the peripheral restriction can refer to decreasing the level of blood-brain barrier penetration. For example, decreasing the level of blood-brain barrier penetration can reduce effects on behavior of a subject. Without wishing to be bound by theory, compounds described herein can be quaternized to increase their selectivity for therapeutic receptors. For example, compounds described herein can be quaternized to increase their selectivity for 5-HT2A over 5-HT1A.

Pharmaceutical Compositions

Pharmaceutical compositions of any of the aforementioned compounds include tablets for oral use containing the compound in a mixture with non-toxic pharmaceutically acceptable excipients. These excipients can be, for example, inert diluents or fillers (e.g., sucrose, sorbitol, sugar, mannitol, microcrystalline cellulose, starches including potato starch, sodium chloride, or lactose); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

In some embodiments, the pharmaceutical composition is prepared, packaged, and/or sold in a formulation suitable for pulmonary administration, e.g., via a nebulizer. Such a formulation can include dry particles that include the active ingredient and which have a diameter in the range from about 0.5 nm to about 7 nm or from about 1 nm to about 6 nm. Such compositions are conveniently in the form of dry powders for administration using a device including a dry powder reservoir to which a stream of propellant can be directed to disperse the powder and/or using a self-propelling solvent/powder dispensing container such as a device including the active ingredient dissolved and/or suspended in a low-boiling propellant in a sealed container. Such powders include particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions can include a solid fine powder diluent such as sugar and are conveniently provided in a unit dose form.

Low boiling propellants generally include liquid propellants having a boiling point of below 65° F. at atmospheric pressure. Generally the propellant can constitute 50% to 99.9% (w/w) of the composition, and active ingredient can constitute 0.1% to 20% (w/w) of the composition. A propellant can further include additional ingredients such as a liquid non-ionic and/or solid anionic surfactant and/or a solid diluent (which can have a particle size of the same order as particles including the active ingredient).

Pharmaceutical compositions formulated for pulmonary delivery can provide an active ingredient in the form of droplets of a solution and/or suspension. Such formulations can be prepared, packaged, and/or sold as aqueous and/or dilute alcoholic solutions and/or suspensions, optionally sterile, including active ingredient, and can conveniently be administered using any nebulization and/or atomization device. Such formulations can further include one or more additional ingredients including, but not limited to, a flavoring agent such as saccharin sodium, a volatile oil, a buffering agent, a surface active agent, and/or a preservative such as methylhydroxybenzoate. Droplets provided by this route of administration can have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder including the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration can, for example, include from about as little as 0.1% (w/w) and as much as 100% (w/w) of active ingredient, and can include one or more of the additional ingredients described herein. A pharmaceutical composition can be prepared, packaged, and/or sold in a formulation suitable for pulmonary administration. Alternately, formulations suitable for buccal administration can include a powder and/or an aerosolized and/or atomized solution and/or suspension including active ingredient. Such powdered, aerosolized, and/or aerosolized formulations, when dispersed, can have an average particle and/or droplet size in the range from about 0.1 nm to about 200 nm, and can further include one or more of any additional ingredients described herein.

Pharmaceutical compositions can be in the form of tablets and/or lozenges made using conventional methods, and can contain from 0.1% to 20% (w/w) active ingredient, the balance including an orally dissolvable and/or degradable composition and, optionally, one or more of the additional ingredients described herein. Tablets can be uncoated or they can be coated by known techniques, optionally to delay disintegration and absorption in the gastrointestinal tract and thereby providing a sustained action over a longer period. For example, the coating can be adapted to release the compound in a predetermined pattern (e.g., in order to achieve a controlled release formulation) or it can be adapted not to release the compound until after passage through the stomach. The coating can be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Additionally or alternatively, a time-delay material such as, e.g., glyceryl monostearate or glyceryl distearate can be incorporated in a tablet.

Solid tablet compositions can include a coating adapted to protect the compound from unwanted chemical changes, (e.g., chemical degradation prior to the release of the compound). The coating can be applied on the solid dosage form in a similar manner to that described in Encyclopedia of Pharmaceutical Technology (eds. J. Swarbrick and J. C. Boylan, 1988-1999, Marcel Dekker, New York).

Pharmaceutical compositions for oral use can also be presented as chewable tablets, or as hard gelatin capsules in which the compound is mixed with an inert solid diluent (e.g., potato starch, lactose, microcrystalline cellulose, calcium phosphate, or kaolin), or as soft gelatin capsules wherein the compound is mixed with water or an oil medium, for example, peanut oil, liquid paraffin, or olive oil. Powders and granulates can be prepared using the ingredients mentioned above under tablets and capsules in a conventional manner using, e.g., a mixer, a fluid bed apparatus or a spray drying equipment.

Powders, dispersible powders, or granules suitable for preparation of an aqueous suspension by addition of water are convenient dosage forms for oral administration of compounds. Formulation as a suspension provides the compound in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

The pharmaceutical composition can also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers, and adjuvants. The formulation and preparation of such compositions are well known to those skilled in the art of pharmaceutical formulation. Formulations can be found in Hayes (Remington: The Science and Practice of Pharmacy, volume I and volume II. Twenty-second edition. Philadelphia, 2012).

Compositions for parenteral use (e.g., intravenous administration) can be provided in unit dosage forms (e.g., in single-dose ampoules), or in vials containing several doses and in which a suitable preservative can be added (see below). The composition can be in form of a solution, a suspension, an emulsion, an infusion device, or a delivery device for implantation, or it can be presented as a dry powder to be reconstituted with water or another suitable vehicle before use. Apart from the compound (e.g., a compound having the structure of formula (I), the composition can include suitable parenterally acceptable carriers and/or excipients. The compound can be incorporated into microspheres, microcapsules, nanoparticles, liposomes, or the like for controlled release. Furthermore, the composition can include suspending, solubilizing, stabilizing, pH-adjusting agents, and/or dispersing agents.

As indicated above, the pharmaceutical compositions according to the invention can be in a form suitable for sterile injection. To prepare such a composition, the compound is dissolved or suspended in a parenterally acceptable liquid vehicle. Among acceptable vehicles and solvents that can be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation can also contain one or more preservatives (e.g., methyl, ethyl or n-propyl p-hydroxybenzoate). In cases where one of the compound is only sparingly or slightly soluble in water, a dissolution enhancing or solubilizing agent can be added, or the solvent can include 10-60% w/w of propylene glycol or the like.

Methods

Provided herein are methods of using a compound or pharmaceutical composition described herein to treat 5-HT2 responsive conditions in a subject. Methods of treating 5-HT2 responsive conditions include administering to a subject in need thereof a therapeutically effective amount of a compound or pharmaceutical composition of the invention.

The exact amount of the compound or composition required for therapeutic effect can vary from subject to subject, depending on the species, age, weight, and general condition of the subject, the severity of the disease, the particular composition, its mode of administration, its mode of activity, and the like. Pharmaceutical compositions in accordance with the present disclosure are typically formulated in dosage unit form for ease of administration and uniformity of dosage. It will be understood, however, that the total daily usage of the compositions of the present disclosure will be decided by the attending physician within the scope of sound medical judgment. The specific therapeutically effective level for any particular subject will depend upon a variety of factors including the particular inflammatory disorder being treated and the severity thereof; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

Compositions described herein can be administered to subjects, such as human patients or, alternatively, to other mammals, such as domesticated animals, cats, dogs, mice, or rats.

Compositions described herein can be administered by any route. In some embodiments, the present compound or pharmaceutical composition thereof is administered by one or more of a variety of routes, including nasal, buccal, oral, by inhalation (e.g., as an oral spray, nasal spray, or aerosol), intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, enteral, vitreal, intratumoral, sublingual; by intratracheal instillation, bronchial instillation, and/or through a portal vein catheter. In some embodiments the composition is administered by systemic intravenous injection. In specific embodiments the composition is administered intravenously and/or orally.

A compound of the invention can be administered in a therapeutically effective amount (e.g., an amount that results in the desired therapeutic effect, e.g., within the therapeutic window between a dose sufficient to reduce inflammation and a dose that elicits a psychoactive effect (about a ten-fold difference)). In some embodiments, the compound is administered in an amount resulting in circulating drug plasma levels of less than 200 ng/mL (e.g., 0.5 to 200 ng/ml, e.g., 1 to 150 ng/mL, 5 to 100 ng/mL, or 10 to 50 ng/ml, e.g., 0.5 to 1 ng/ml, 1 to 2 ng/mL, 2 to 3 ng/ml, 3 to 4 ng/mL, 4 to 5 ng/mL, 5 to 10 ng/mL, 10 to 50 ng/mL, 50 to 100 ng/ml, 100 to 150 ng/mL, or 150 to 200 ng/ml, e.g., about 0.5 ng/ml, 1 ng/ml, 2 ng/ml, 5 ng/mL, 10 ng/ml, 20 ng/mL, 25 ng/mL, 50 ng/mL, 75 ng/mL, 100 ng/mL, 120 ng/ml, 150 ng/mL, or 200 ng/mL), e.g., in a human subject. In some embodiments, the circulating drug plasma level of the compound is below the limit of detection (e.g., 0.1 ng/ml or less). In some embodiments, a therapeutically effective amount of the compound can be less than about 2000 μg/kg body weight (e.g., less than 1000 μg/kg, less than 500 μg/kg, less than 100 μg/kg, or less than 50 μg/kg body weight, e.g., from 100 to 2000 μg/kg body weight, e.g., from 100 to 500 μg/kg, from 500 to 1000 μg/kg, from 1000 to 1500 μg/kg, or from 1500 to 1000 μg/kg, e.g., about 500 μg/kg, about 1000 μg/kg, about 1500 μg/kg, or about 2000 μg/kg).

In certain embodiments, compositions in accordance with the present disclosure can be administered at dosage levels sufficient to deliver from about 0.0001 μg/kg to about 1 mg/kg, from about 0.01 μg/kg to about 500 μg/kg, from about 0.1 μg/kg to about 400 μg/kg, from about 0.5 μg/kg to about 30 μg/kg, from about 0.01 μg/kg to about 10 μg/kg, from about 0.1 μg/kg to about 10 μg/kg, or from about 1 μg/kg to about 25 μg/kg, of subject body weight per day, one or more times a day, to obtain the desired therapeutic effect. The desired dosage can be delivered three times a day, two times a day, once a day, every other day, every third day, every week, every two weeks, every three weeks, or every four weeks. In some embodiments, the compound is administered at a frequency of one to three times per week (e.g., once per week, twice per week, three times per week, four times per week, five times per week, six times per week, seven times per week, or more, e.g., once daily, twice daily, three times daily, etc.). In some embodiments, the compound is administered intermittently, e.g., every other day, every other week, once per month, etc. In certain embodiments, the desired dosage can be delivered using multiple administrations (e.g., two, three, four, five, six, seven, eight, nine, ten, eleven, twelve, thirteen, fourteen, or more administrations).

Compositions described herein can be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Pharmaceutical compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that improve their bioavailability, reduce and/or modify their metabolism, inhibit their excretion, and/or modify their distribution within the body.

It will further be appreciated that compounds or compositions utilized in combination can be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The term "subject" or "patient" refers to any organism to which aspects of the invention can be administered, e.g., for experimental, diagnostic, prophylactic, and/or therapeutic purposes. Typical subjects to which compounds of the disclosure can be administered will be animals, particularly mammals, such as primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

As used here, a subject "in need thereof" refers to a subject that has the disorder or disease to be treated or is predisposed to or otherwise at risk of developing the disease or disorder.

Methods of Screening Compounds

Provided herein are methods for testing and/or for screening compounds for anti-inflammatory and/or anti-ROS activity. Without wishing to be bound by theory, a mutation of N343 can be generated to test and/or screen compounds for anti-inflammatory and/or anti-ROS activity. For example, the mutation comprises a N343 to A343 receptor mutation (N343A). This N343A mutant receptor can be used to screen compounds for anti-inflammatory activity. In embodiments, the N343A mutant can be incorporated into a peroxidase proximity labeling assay to identify effectors relevant to anti-inflammatory and/or anti-ROS activity. For example, the receptor mutant can be used in an in vitro TNF-alpha administration assay. In embodiments, the mutant receptor can be used in an in vitro assay examining oxidative stress response. In each of these cases, without wishing to be bound by theory, the native receptor confers full anti-inflammatory activity, and the mutant reduces anti-inflammatory activity of certain molecules depending on the nature of the 5- or 4-position of phenethylamines and tryptamines, respectively.

Psychological Conditions

In particular embodiments, the 5-HT2 responsive condition to be treated is a psychological condition. Disclosed herein are methods of treating psychological conditions. The psychological condition can be any psychological condition described herein. In some embodiments the psychological condition comprises depression, anxiety, addiction, post-traumatic stress disorder (PTSD), an eating disorder, or compulsive behavior. In some embodiments, the psychological condition can be depression. The psychological condition can also be anxiety. The anxiety can be experienced by a subject who is receiving palliative care or is enrolled in a hospice program. In certain embodiments, the subject who is experiencing anxiety has symptoms such as hypervigilance, fatigue, racing thoughts, irritability, excessive worry, and/or fear.

A subject with a psychological condition can be diagnosed by a clinician, a physician, or a therapist. The subject can be diagnosed with a psychological condition by evaluation of the subject's symptoms by a physician, clinician, or therapist based on a physical examination. For example, a blood test can be used to evaluate blood concentration levels of certain biomarkers such as hormones, calcium, vitamin D, electrolytes, and iron in diagnosing depression. Additionally or alternatively, for patients with a possible depression condition a depression screening test can be performed by the physician, clinician, or therapist to aid in the diagnosis of depression. The depression screening test can be the Patient Health Questionnaire-9 (PHQ-9), the Beck Depression Inventory (BDI), the Zung Self-Rating Depression Scale, the Center for Epidemiological Studies Depression Scale (CES-D), the Hamilton Rating Scale for Depression (HRSD), or the Montgomery-Asberg Depression Rating Scale (MADRS-C). In some embodiments, the methods described herein can be used to treat psychosomatic pain conditions. In some embodiments, the psychosomatic pain condition can be fibromyalgia, chronic fatigue, migraines, or back pain.

In some embodiments, the patient is being treated for depression with a compound of formula (I). The patient can have their symptoms of depression evaluated using a depression screening test. The symptoms of depression can be evaluated by a clinician using the Clinical Global Impression (CGI) rating. The depression screening test can be the Patient Health Questionnaire-9 (PHQ-9), the Beck Depression Inventory (BDI), the Zung Self-Rating Depression Scale, the Center for Epidemiological Studies Depression Scale (CES-D), the Hamilton Rating Scale for Depression (HRSD), and/or the Montgomery-Asberg Depression Rating Scale (MADRS). The patient being treated for depression with a compound of formula (I) can have their symptoms of depression evaluated using the Montgomery-Asberg Depression Rating Scale (MADRS-C). In some embodiments, the patient evaluated using the MADRS-C by a clinician, physician, or third-party rater. In certain embodiments, the patient can self-evaluate using the MADRS. The patient's score obtained using the MADRS-C can be decreased compared to the score before treatment. The patient's score can decrease by at least 50% compared to the score before treatment. The patient's score obtained using the MADRS-C can be less than 10. In some embodiments, the decrease in the patient's score using the MADRS-C is decreased for 1 week after treatment. In certain embodiments, the decrease in the patient's score using the MADRS-C is decreased for 4 weeks after treatment. In particular embodiments, the patient's score using the MADRS-C is decreased for more than 4 weeks after treatment.

In certain embodiments, the patient is being treated for anxiety with a compound of formula (I). The patient can have their symptoms of anxiety evaluated using an anxiety screening test. The anxiety screeningtest can be the Zung Self-Rating Anxiety Scale, the Hamilton Anxiety Scale, the Beck Anxiety Inventory, the Social Phobia Inventory, the Penn State Worry Questionnaire, the Yale-Brown Obsessive-Compulsive Scale, or the—General Anxiety Disorder-7. In some embodiments, the patient's anxiety score using any one of these screening tests decreases in comparison to the patient's score before receiving treatment. In certain embodiments, the patient's anxiety score using any one of the above screening tests decreases by 50% in comparison to the patient's score before receiving treatment. In embodiments, the patient meets fewer criteria for anxiety as described by the Diagnostic and Statistical Manual of Mental Disorders in comparison before receiving treatment.

In one embodiment, the methods of the invention are used to treat psychological conditions, e.g., depression, anxiety, PTSD, an eating disorder, and compulsive behavior, by administering a compound of formula (I) as needed to treat the symptoms associated with the psychological condition. In embodiments, the methods of the invention are used to treat psychological conditions by administering at least one of the compounds described herein to a subject in need thereof.

Neurological Injuries

In particular embodiments, the 5-HT2 responsive condition to be treated is a neurological injury. Also disclosed herein are methods of treating a neurological injury. The neurological injury can be any neurological injury. In some embodiments, the neurological injury is a stroke, a traumatic brain injury, or a spinal cord injury. The methods of treating a neurological injury described herein can reduce acute inflammation. In certain embodiments, hippocampal hyperactivity is reduced. Also, the methods described herein for treating a neurological injury can be administered in combination with a behavioral, physical, or speech therapy.

In particular embodiments, the methods of the invention are used to treat a neurological injury, e.g., stroke, traumatic brain injury, and spinal cord injury, by administering a compound of formula (I) as needed to pain, inflammation, and/or other symptoms associated with the neurological injury. In embodiments, the methods of the invention are used to treat neurological injuries by administering at least one of the compounds described herein to a subject in need thereof.

Degenerative Diseases

In embodiments, the 5-HT2 responsive condition to be treated is a degenerative disease. Also discussed herein are methods of treating a degenerative disease. The degenerative disease can be any degenerative disease. In some embodiments, the degenerative disease comprises diabetic retinopathy, macular degeneration, and Alzheimer's Disease.

In embodiments, the methods of the invention are used to treat degenerative diseases by administering at least one of the compounds described herein to a subject in need thereof.

Inflammatory Conditions

In particular embodiments, the 5-HT2 responsive condition to be treated is an inflammatory condition. An inflammatory condition in a subject can be treated with a compound of formula (I) using the methods of the invention. The inflammatory condition to be treated can be a lung inflammation (e.g., chronic obstructive pulmonary disease (COPD)), neuroinflammation (e.g, Alzheimer's disease), chronic inflammation, rheumatoid arthritis, atherosclerosis, psoriasis, type II diabetes, inflammatory bowel disease, Crohn's disease, conjunctivitis, multiple sclerosis, and/or septicemia.

In one embodiment, inflammation is treated by administering a compound of formula (I) as needed to treat (i) acute attacks of inflammation (e.g., inflammatory bowel disease), or (ii) chronic inflammatory conditions (e.g., arthritis). In embodiments, the methods of the invention are used to treat inflammatory conditions by administering at least one of the compounds described herein to a subject in need thereof.

Chronic Pain

In particular embodiments, the 5-HT2 responsive condition to be treated is chronic pain. A disorder of condition associated with chronic pain can be treated with a compound of formula (I) using the methods of the invention. The chronic pain can result from post-operative pain, tension headaches, chronic lower back pain, fibromyalgia, nephropathy, multiple sclerosis, shingles, complex regional pain syndrome, cephalic pain, or sciatica. The chronic pain can arise from an operation. The chronic pain can also be pain associated with a particular disease or condition such as nephropathy, multiple sclerosis, shingles, or complex regional pain syndrome. One particular disorder or condition associated with cephalic pain can be treated with a compound of formula (I) using the methods of the invention. As used herein, a disorder or condition associated with cephalic pain is a disorder or condition which has as one of its symptoms cephalic/head pain (e.g., headache). Examples of such disorders or conditions include trigeminal autonomic cephalalgias such as episodic and chronic cluster headache (CH), episodic and chronic paroxysmal hemicrania (PH), and short-lasting unilateral neuralgiform headache attacks with conjunctival injection and tearing (SUNCT). Other examples of disorders or conditions which can be treated according to the present invention include vascular headaches (e.g., migraine headaches), tension headaches, headaches associated with the use of a substance (e.g., triptans such as sumatriptan, benzodiazepines such as alprazolam, analgesics such as ibuprofen, ergots such as ergotamine, opioids such as morphine, recreational drugs such as caffeine, nicotine, alcohol, and hormone replacement therapy containing, for example, estrogen) or its withdrawal. Yet additional examples of disorders or conditions associated with cephalic pain include miscellaneous headache unassociated with a structural lesion, headache associated with a nonvascular intracranial disorder, headache associated with a non-cephalic infection, headache associated with a metabolic disorder, headache associated with a disorder of the cranium, neck, eyes, nose, sinuses, teeth, mouth, or other facial or cranial structure, nerve trunk pain and deafferentation pain.

In embodiments, the methods of the invention are used to treat chronic pain by administering at least one of the compounds described herein to a subject in need thereof.

EXAMPLES

The following examples are put forth so as to provide those of ordinary skill in the art with a description of how the compositions and methods claimed herein can be performed, made, and evaluated, and are intended to be purely exemplary of the invention and are not intended to limit the scope of what the inventor regards as his or her invention.

Example 1. Engagement of 5-HT2A Receptor Residues and New Ligands for Anti-Inflammatory Activity Without wishing to be bound by theory, specific engagement of Asparagine 343 (position 6.55) of the human serotonin 5-HT2A receptor by a small molecule ligand can be necessary, in instances, for anti-inflammatory activity of drugs with affinity for the 5-HT2A receptor.

For example, compounds that engage N343 of 5-HT2A can be used as anti-inflammatory medications for the treatment of diseases including but not limited to asthma, arthritis, inflammatory bowel disease, psoriasis. These compounds can also be used as medications to treat degenerative diseases, for example, but not limited to diabetic retinopathy, macular degeneration, Alzheimer's Disease.

Without wishing to be bound by theory, current drugs acting as anti-inflammatoires at the 5-HT2A receptor do not directly engage with N343 (6.55) of the 5-HT2A receptor. For example, direct engagement of this residue through hydrogen bonding with the ligand itself can provide increased efficacy and/or potency of anti-inflammatory/anti-ROS (reactive oxygen species) effects for therapeutic benefit. Without wishing to be bound by theory, the compounds can move the electron acceptor oxygen about 3 Å or less away from the electron nitrogen donor. For example, the compounds can move the electron acceptor oxygen to directly hydrogen bond with the electron donor nitrogen.

Figure 2:
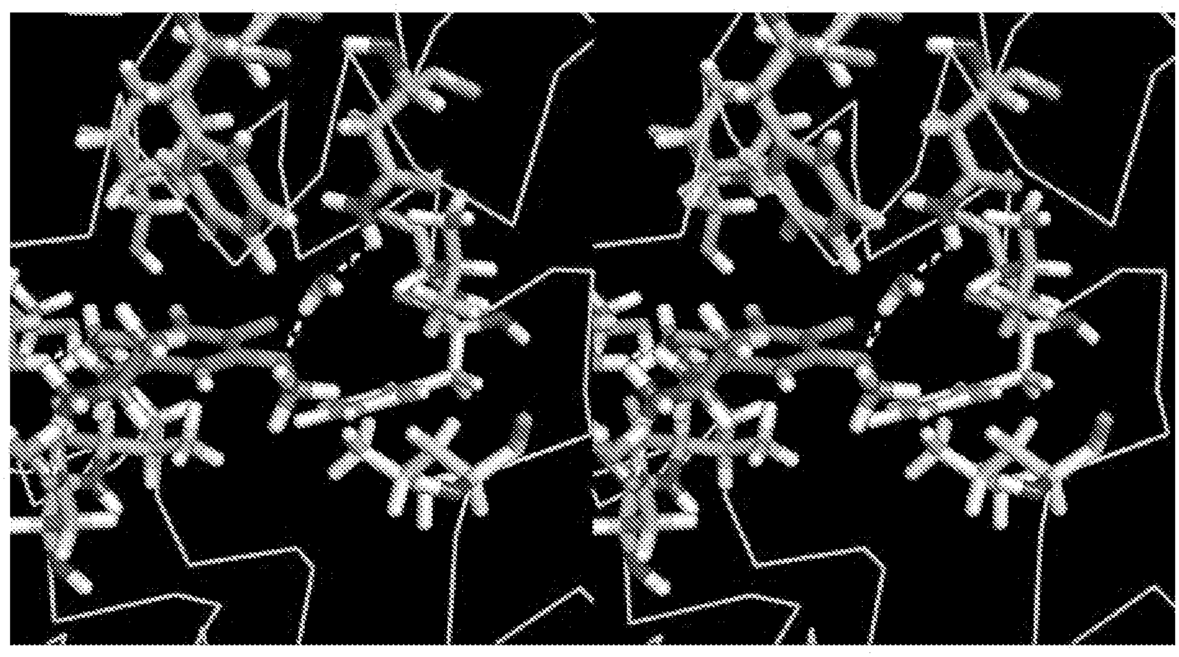
FIG. 2 shows an in silico diagram of when a water molecule is placed into this pocket, the oxygen of the methoxy can hydrogen bond to the water, and the water to N343.

Example 2. Within the Human 5-HT2A Receptor, Engagement of the TM6 Asparagine at Position 343 (6.55) can be Critical for Full Anti-Inflammatory Efficacy. New Chemical Entities can Specifically Engage this Residue for Anti-Inflammatory Drug Design Purposes Upon the discovery and publication of the crystal structure of the h5-HT2A receptor bound to 25CN—NBOH (Kim et al. 2020), we noticed that there was nothing available in the vicinity of the 5-methoxy for it to hydrogen bond to, which was odd and not informative as to how DOx (4-substituted-2,5-dimethoxyamphetamine) compounds engage the receptor. Instead, there was a gap between the ligand and the nearest polar residue (FIG. 1). Without wishing to be bound by theory, placing a water molecule in that space can provide a bridge to form a hydrogen bond between the TM6 N343 and 5-methoxy oxygen. Indeed, one placed there shows it fits exactly for this interaction (FIG. 2). For example, the orientation in the binding pocket and the engagement of the receptor in the active confirmation of the receptor of the DOx/2Cx compounds can be validated experimentally.

Figure 4:
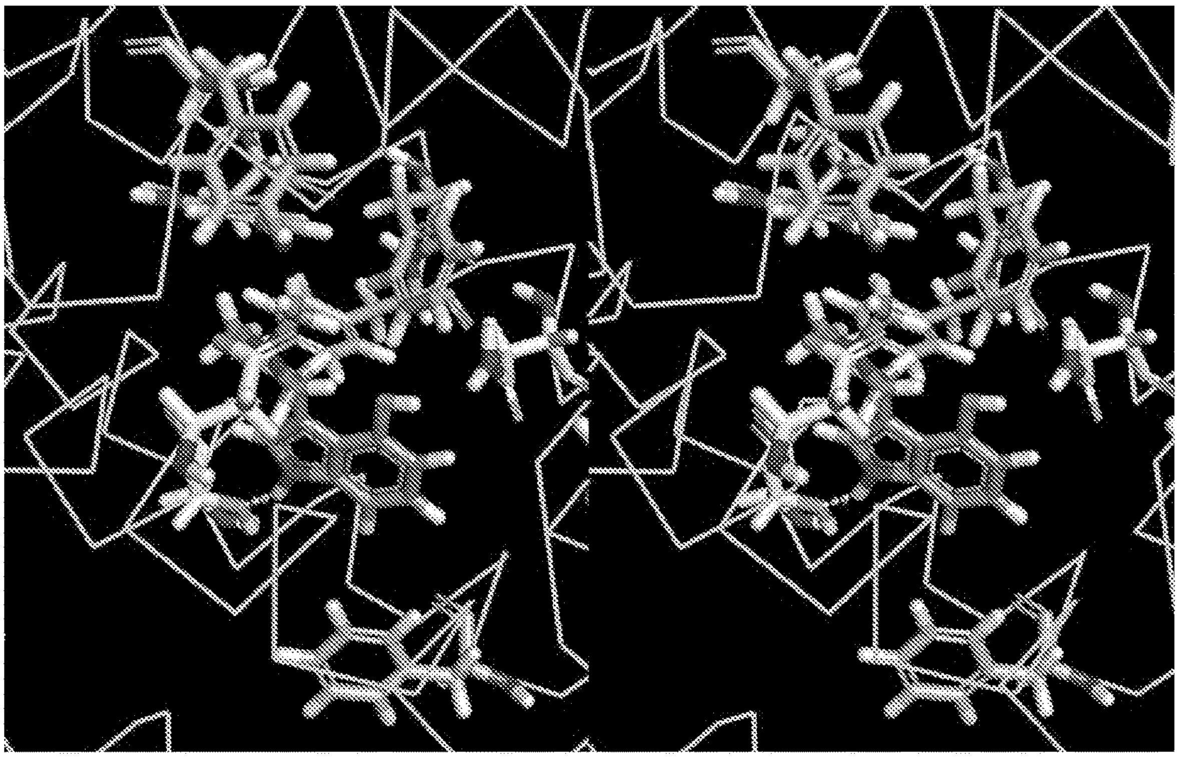
FIG. 4 shows an in silico diagram of psilocin placed into the binding pocket corresponding to the position that the indole ring of LSD occupies based on the recent X-ray crystal structure of HT2A complexed with LSD (See PMID: 32946782; See also Kim K, et al. Structure of a Hallucinogen-Activated Gq-Coupled 5-$HT_{2A}$ Serotonin Receptor. Cell. 2020 Sep. 17; 182 (6): 1574-1588). The 4-OH of psilocin pokes into a similar empty pocket. A water placed in the empty pocket allows for a similar hydrogen bond bridge to N343.

We determined that DOx/2Cx structures with a modified or missing 5-methoxy have reduced anti-inflammatory activity (FIG. 3). Further, the experimental data also showed that for tryptamines, the absence of a 4-OH leads to loss of all anti-inflammatory efficacy. Without wishing to be bound by theory, the 5-methoxy of the DOx/2Cx compounds can engage residues in the binding pocket similar to those that engage the 4-OH of tryptamines, although the residues engaged by tryptamines have not been elucidated because the crystal structure of a tryptamine in the 5-HT2A receptor has not yet been published. Psilocin manually placed into the binding pocket, however, based on the orientation of the indole core of LSD from the published crystal structure (Kim et al. 2020) shows a similar result, with the 4-OH projecting onto the same large pocket (FIG. 4). Thus, without wishing to be bound by theory, a water molecule also must be present there to form a hydrogen bond bridge from the oxygen to N343.

The SAR results as shown in FIG. 3 are consistent with engagement of TM6 N343 by the 5-methoxy or 4-OH of DOx/2Cx or tryptamines, respectively, through a hydrogen bond bridge with a water molecule to produce the conformational change to recruit anti-inflammatory effectors to the activated receptor.

If experimentally validated, ligands able to engage the TM6 N343 directly, without the intermediacy of a structural water, to produce the correct TM6 helical rotation and conformational change for recruitment of anti-inflammatory effector pathways can be a critical parameter for the development of NCEs, either through rational drug design or high throughput in silico screening efforts.

Non-Limiting Example of Testing:

The h5-HT2A N343 A mutant can be generated. Replacing the asparagine with the small methyl of an alanine can remove any hydrogen bond donor capacity from this region of the receptor pocket, and without wishing to be bound by theory, not require the recruitment of a water molecule to this space. Without these features, the affinity and/or efficacy of traditional 5-methoxy DOx/2Cx and 4-OH tryptamine drugs is predicted to be reduced in the mutant compared to the wild type. The affinity of drugs whose structures lack these moieties is expected not to be changed (e.g psilocin vs DMT (N,N-dimethyltryptamine); 2,4-DMA (2,4-dimethoxyamphetamine) vs 2,4,5-TMA (2,4,5-trimethoxyamphetamine). One test will be to determine whether traditional DOx/2Cx and 4-OH tryptamines lose anti-inflammatory or anti-oxidant efficacy in in vitro cell based systems (e.g. native or mutant receptor expressing cells challenged with peroxide in a priming context). If this engagement is an important feature of the MoA, drugs such as DOI (2,5-dimethoxy-4-iodoamphetamine) and psilocin can have reduced potency and/or efficacy, but the partial efficacy of 2,4-TMA would not change. This mutant receptor can be cloned into a mammalian cell expression vector.

Figure 5:
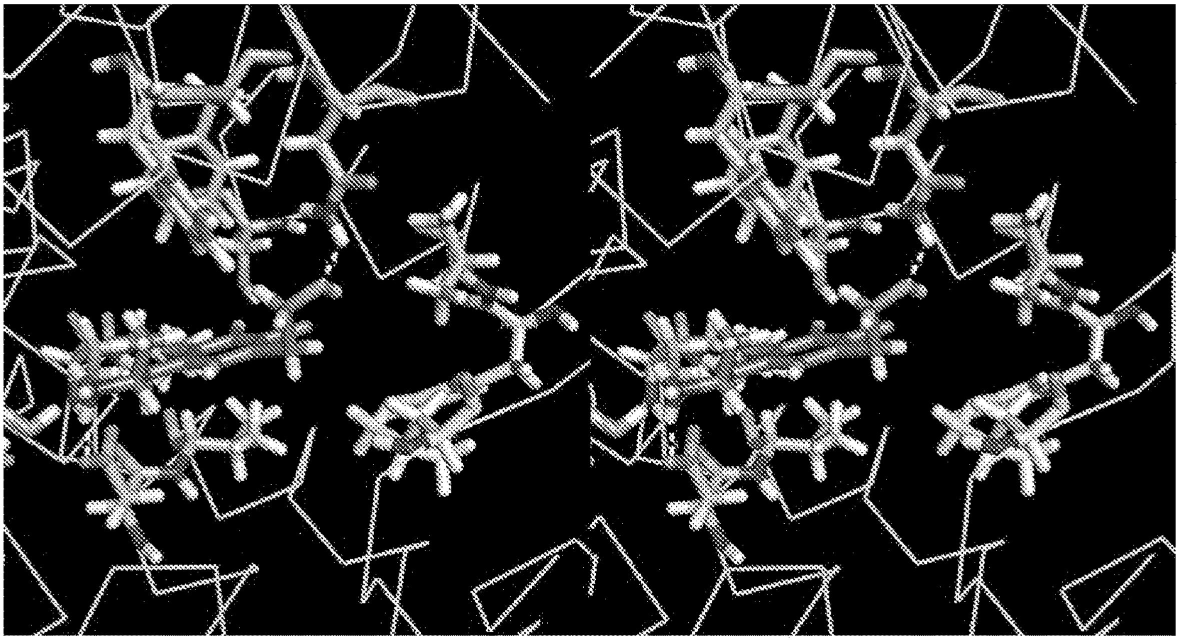
FIG. 5 shows an in silico diagram of the oxygen of a 5-hydroxyethyl on a DOx/2Cx that can directly hydrogen bond to N343.
Figure 6:
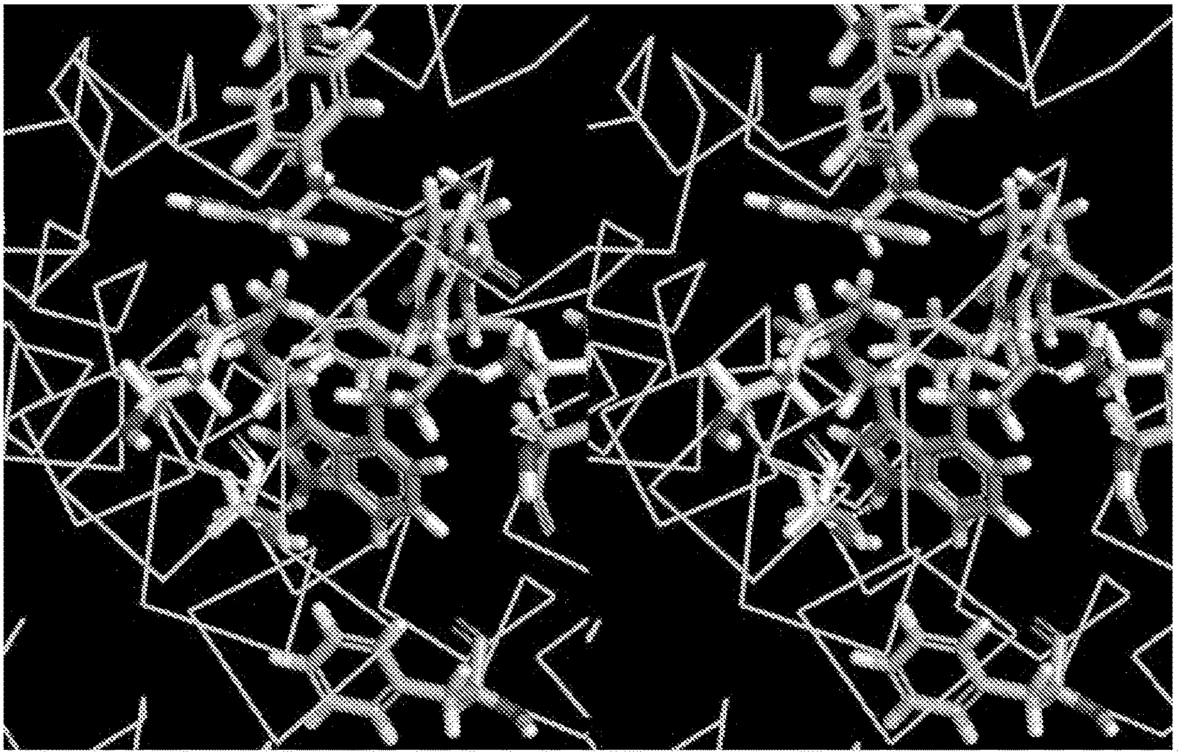
FIG. 6 shows an in silico diagram of a 4-hydroxyethyl on a tryptamine also places the oxygen within hydrogen bonding distance with N343.

Without wishing to be bound by theory, chemical entities can be generated which incorporate structural features to engage N343 directly without the use of a water molecule bridge (FIGS. 5-6). Without wishing to be bound by theory, compounds which can engage N343 directly can comprise 2-methoxy-5-hydroxyethyl-4-methylamphetamine, 2-methoxy-5-hydroxyethyl-4-methylphenethylamine, and 4-(2-hydroxyethyl)-N,N-DET (see herein). These compounds can have improved potencies and/or efficacies relative to the parent molecules (e.g. DOM, DET) for anti-inflammatory effects in the native receptor, but reduced in comparison to the mutant receptor. The 2-methoxyethyl versions of these compounds can also be generated to directly engage N343.

Further Possibilities with these Compounds:

1) Replacing the 5-methoxy with a 5-(2-hydroxyethyl) in the DOx/2Cx can decrease blood brain barrier penetration and reduce behavioral liability.
2) For tryptamines, the 4-(2-hydroxyethyl) (or 4-(2-methoxyethyl)) can provide improved selectivity for 5-HT2 over 5-HT1A receptors because the 5-HT1A receptor does not have a hydrogen bond donor residue at position 6.55.
3) Generating a quaternary amine of the 4-hydroxyethyl tryptamine can keep it out of the brain (in addition to providing greater selectivity over 5-HT1A). →Potent peripherally restricted anti-inflammatory with enhanced selectivity for 5-HT2A/5-HTIA.

ADDITIONAL CONSIDERATIONS

Without wishing to be bound by theory, incorporating the mutant N343A receptor into the planned peroxidase proximity labeling assays can provide another path towards identification of effectors recruited to the signalplex relevant to anti-inflammatory activity. For example, N343A receptor vs Wild Type receptor for DOI→Pathways recruited to DOI in the wild type but not mutant are relevant.

Convergent effectors identified by non-limiting, exemplary experiments described herein can be candidates for involvement in anti-inflammatory mechanisms.

Non-limiting Compounds of aspects of the invention:

a) NCCC1=C(OC)C=C(C)C(CCO)=C1

2-(5-(2-aminoethyl)-4-methoxy-2-methylphenyl) ethan-1-ol b) NC(C)CC1=C(OC)C=C(C)C(CCO)=C1

2-(5-(2-aminopropyl)-4-methoxy-2-methylphenyl) ethan-1-ol c) OCCC1=C$_2$C(NC=C$_2$CCN(CC)CC)=CC=C1

2-(3-(2-(diethylamino)ethyl)-1H-indol-4-yl) ethan-1-ol (a)

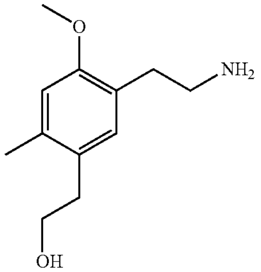

-continued (b)

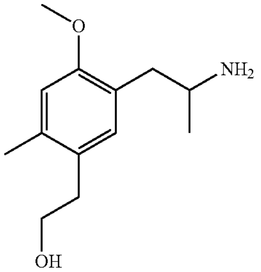

(c)

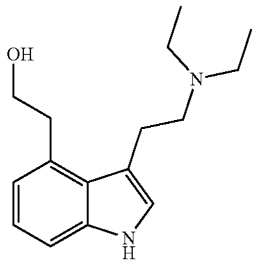

Example 3

Figure 8:
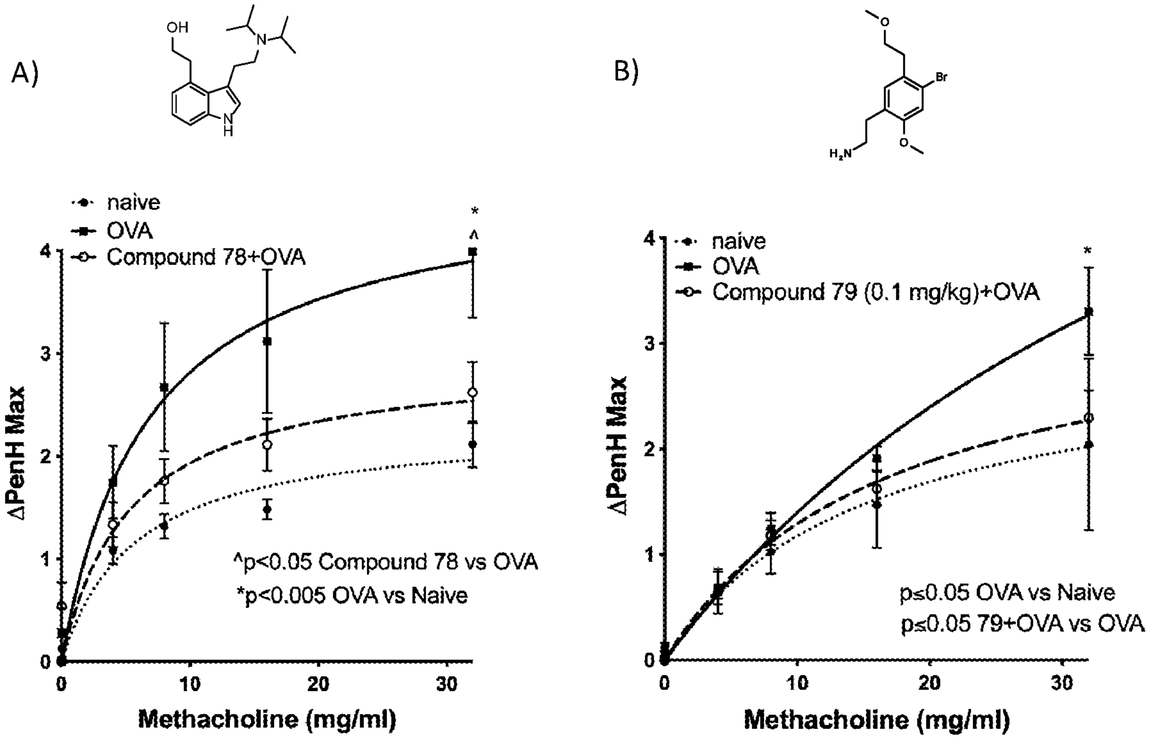
FIG. 8 shows graphs of 4-hydroxyethyl-DIPT tested at a dose of 0.5 mg/kg (Panel A) and 2-methoxy-4-bromo-5-methoxyethylphenethylamine administered at 0.1 mg/kg (Panel B) in a rat model of allergic asthma.

4-hydroxyethyl-DIPT, and 2-methoxy-4-bromo-5-methoxyethylphenethylamine were tested for their ability to prevent increases in PenH in a rat model of allergic asthma (the OVA sensitization and exposure model) (FIG. 8). A reduction in PenH for the drug treatment+OVA compared to the OVA alone treatment represents anti-inflammatory activity. 4-hydroxy-DIPT was tested at a dose of 0.5 mg/kg (Panel A), and 2-methoxy-4-bromo-5-methoxyethylphenethylamine was administered at 0.1 mg/kg (Panel B).

Figure 9:
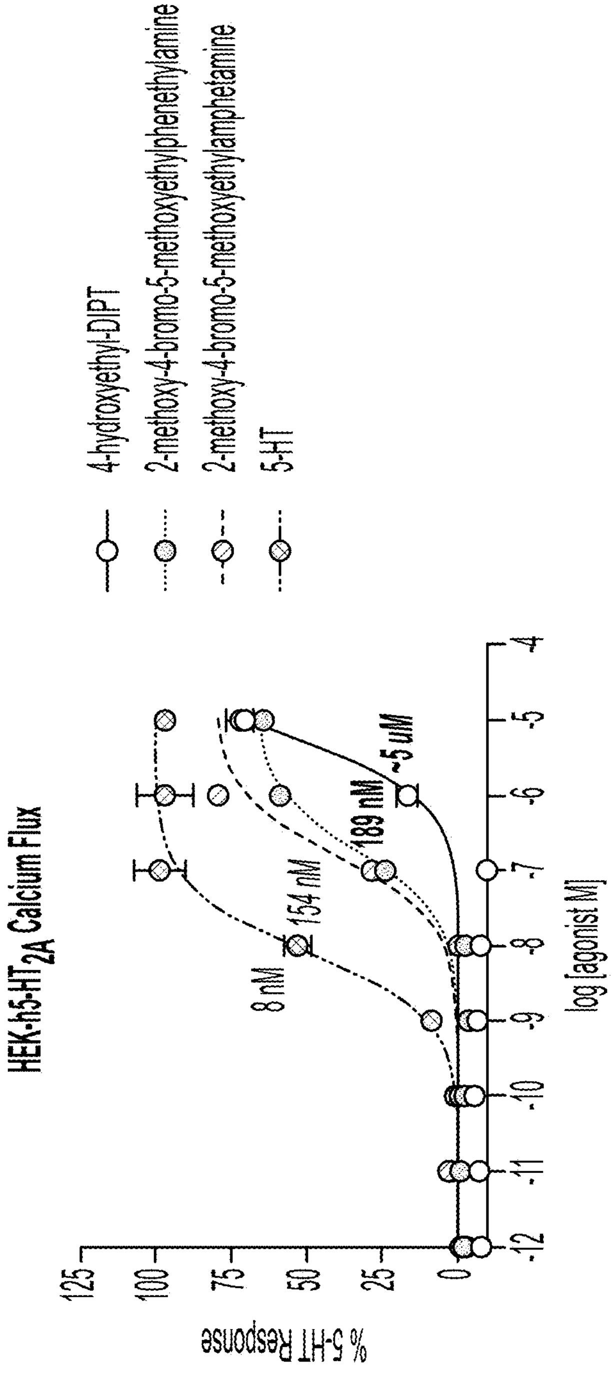
FIG. 9 shows a graph of HEK-h5-$HT_{2A}$ Calcium Flux.

Calcium flux dose response experiments were performed in HEK cells stably transfected with human 5-HT2A receptors for the three drugs compared to serotonin (5-HT) (FIG. 9). All three are agonists at the 5-HT2A receptor with respect to calcium flux. The EC50 values for each curve are shown in the graph.

Example 4

Non-Limiting Examples of Binding Affinity for 5-HT2A Receptor

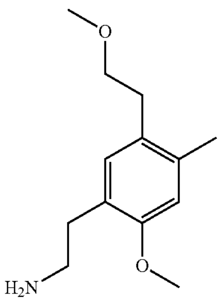 [SMILES: COCCc1cc(CCN)c(OC)cc1C]

$K_i$=6.34×10^10−7 nM against [3]-ketanserin in radioligand displacement binding assay. The Ki value determined represents the concentration of drug where half of the binding sites available in the prep are occupied by the test drug.

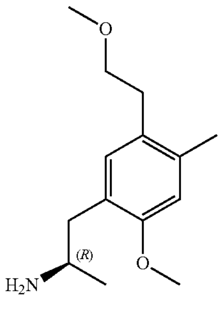

$K_i$=3.45×10^−6 nM against [3]-ketanserin in radioligand displacement binding assay. The Ki value determined represents the concentration of drug where half of the binding sites available in the prep are occupied by the test drug.

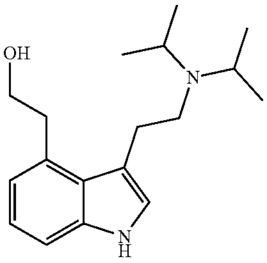

Without wishing to be bound by theory, 4-hydroxyethyl-DIPT interacts with 5-HT2A receptors.

Non-Limiting, Exemplary Experimental Protocol for Radioligand Binding Assay

HEK cells stably expressing human 5-HT2A receptors were cultured in DMEM (Gibco, Cat. #10569-010) supplemented with 10% (v/v) fetal bovine serum (Gibco, Cat. #16000-044; Lot #2344386RP), 100 units/mL penicillin, and 100 mg/mL streptomycin, 100 μg/mL Zeocin™, and maintained in a humidified atmosphere at 37° C. and 5% $CO_2$. The cells were then serum-starved in DMEM (Gibco, Cat. #10569-010) for 12 hours. Membranes were prepared by scraping and homogenizing cells in DMEM (about 5 mL per 15-cm dish) on ice and centrifuged at 2,000×g for 10 minutes at 4° C. Cells were resuspended in cold binding buffer (50 mM Tris-HCl, 10 mM $MgCl_2$, 0.1 mM EDTA, pH 7.4), homogenized, and centrifuged again. After resuspension in cold binding buffer, 1 mL aliquots were distributed to pre-chilled 1.5 mL microcentrifuge tubes and centrifuged at 13,000 rpm for 20 minutes at 4° C. Supernatant was aspirated immediately and pellets stored at −80° C. until needed. On the following day, one pellet was resuspended in 1 mL cold binding buffer and protein concentration quantified using a Quick Start™ Bradford Protein Assay Kit 2 (Bio-Rad, Cat. #500-0202). On day of assay, the following components were diluted in cold binding buffer in a 96 well 2 mL deep well polypropylene plate and incubated at room temperature on a platform rocker for 1 hour: 25 μg membrane preparation, [3H]-ketanserin hydrochloride (1 nM, final concentration) (PerkinElmer Life Sciences, Part #NET791025UC), and a range of 7 concentrations of drug (1×10^−11-1×10^−5 M, final concentration). Mianserin (100 μM) was used to define nonspecific binding in a separate reaction. Each drug concentration point was tested in triplicate. Samples were filtered onto a 0.25% polyethylenimine-coated UniFilter-96 GF/C microplate (PerkinElmer Life Sciences, Part #6055690) using a PerkinElmer FilterMate™ cell harvester and counted in MicroScint™-20 cocktail (PerkinElmer Life Sciences, Part #6013621) on a PerkinElmer Microbeta2 System at 57% efficiency. Raw data were exported to an Excel spreadsheet and nonspecific baseline subtracted. Ki values were generated using the GraphPad Prism 9.3.1 "One site-Fit Ki" function (GraphPad Software, San Diego, CA).

OTHER EMBODIMENTS

All publications, patents, and patent applications mentioned in this specification are herein incorporated by reference to the same extent as if each independent publication or patent application was specifically and individually indicated to be incorporated by reference.

Although the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claims.

Other embodiments are within the claims.

What is claimed is:

1. A compound of formula (I):

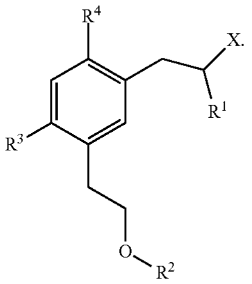

(I)

wherein,

X is $NH_2$, $NH(CH_3)$, $N(CH_3)_2$, or $N(CH_3)_3$;

$R^1$ is H or $CH_3$;

$R^2$ is H or $CH_3$;

$R^3$ is halogen, trifluoromethyl, CN, substituted $C_{1-8}$ alkyl substituted $C_{2-8}$ alkenyl, substituted $C_{1-8}$ alkoxy, and $C_1$-$C_8$ alkylthio; and $R^4$ is H, OH, $OCH_3$, or $OCH_2CH_3$, or a pharmaceutically acceptable salt thereof.

2. The compound claim 1, wherein $R^3$ is selected from bromo, iodo, CN, $—CH_3$, $—CH_2CH_3$, $—CH(CH_3)_2$, $—CH_2CH(CH_3)_2$, $—CH_2CH_2CH(CH_3)_2$, $—CH_2CH_2CH_2CH_3$, $—C(CH_3)_3$, $—CH_2C(CH_3)_3$, $—OCH(CH_3)_2$, $—OC(CH_3)_3$, and $C_1$-$C_8$ alkylthio, or a group selected from:

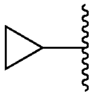

,

-continued

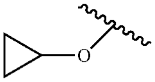
,

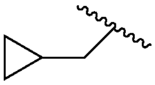
,

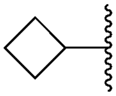
,

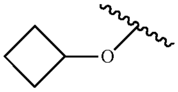
, and

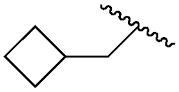
.

3. The compound of claim 1, wherein the compound of formula (I) is selected from any one of compounds 1-4:

(1)

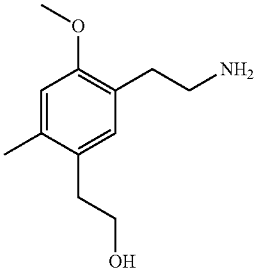

(2)

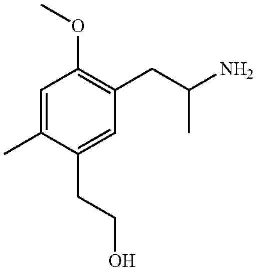

(3)

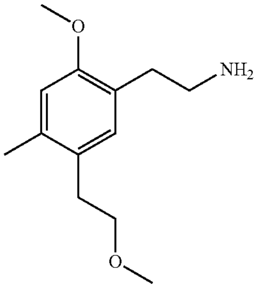

-continued (4)

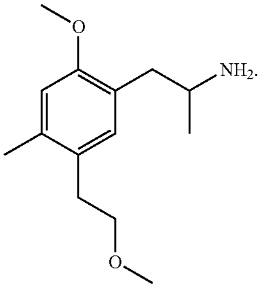

4. A compound of formula (II):

(II)

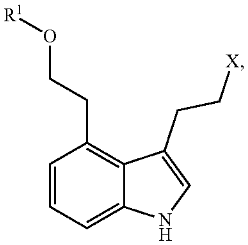

wherein, $R_1$ is H or $CH_3$;

X is $N(R_2)$ $(R_3)$ or $N(R_2)$ $(R_3)$ $(CH_3)$; and each of $R_2$ and $R_3$ are, independently, selected from $—CH_3$, $—CH_2CH_3$, $—CH(CH_3)_2$, and $—CH_2CH(CH_3)_2$, or a pharmaceutically acceptable salt thereof.

5. The compound of claim 4, wherein the compound of formula (II) is selected from any one of compounds 5-8:

(5)

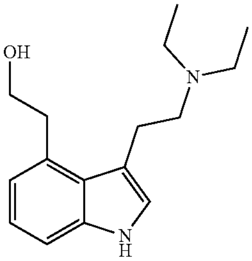

(6)

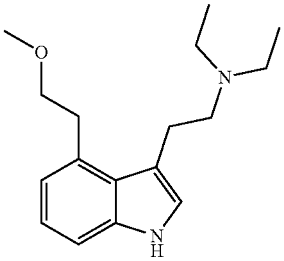

-continued (7)

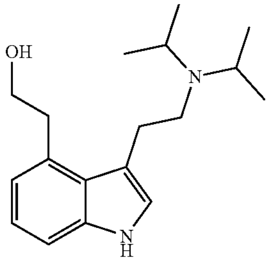 [SMILES: CC(C)N(CCc1c[nH]c2cccc(CCO)c12)C(C)C]

(8)

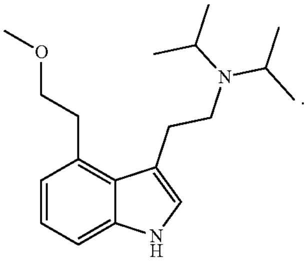

6. A pharmaceutical composition comprising the compound of claim 1 and a pharmaceutically acceptable excipient.

7. The pharmaceutical composition of claim 6, wherein the pharmaceutical composition is formulated for oral, intranasal, or pulmonary administration.

8. A method of treating an inflammatory disorder in a subject in need thereof, the method comprising administering to the subject a therapeutically effective amount of the compound of claim 1.

9. The method of claim 8, wherein the inflammatory disorder is selected from the group consisting of asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, Alzheimer's disease, and conjunctivitis.

10. A method of treating a psychological condition in a subject in need thereof, the method comprising administering to the subject a therapeutically effective amount of the compound of claim 1.

11. The method of claim 10, wherein the psychological condition is depression, anxiety, addiction, post-traumatic stress disorder, an eating disorder, or compulsive behavior.

12. A method of treating chronic pain in a subject in need thereof, the method comprising administering to the subject a therapeutically effective amount of the compound of claim 1.

13. The method of claim 8, wherein the compound is administered orally, intranasally, or by inhalation.

14. A method of treating an inflammatory disorder in a subject in need thereof, the method comprising administering to the subject a therapeutically effective amount of the compound of claim 4.

15. The method of claim 14, wherein the inflammatory disorder is selected from the group consisting of asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, Alzheimer's disease, and conjunctivitis.

16. A method of treating a psychological condition in a subject in need thereof, the method comprising administering to the subject a therapeutically effective amount of the compound of claim 4.

17. The method of claim 16, wherein the psychological condition is depression, anxiety, addiction, post-traumatic stress disorder, an eating disorder, or compulsive behavior.

18. A method of treating chronic pain in a subject in need thereof, the method comprising administering to the subject a therapeutically effective amount of the compound of claim 4.

* * * * *